(12) United States Patent
Abe et al.

(10) Patent No.: US 11,395,583 B2
(45) Date of Patent: *Jul. 26, 2022

(54) ENDOSCOPE LIGHT EMITTING DEVICE, ENDOSCOPE USING SAME, AND FLUORESCENCE IMAGING METHOD

(71) Applicant: Panasonic Intellectual Property Management Co., Ltd., Osaka (JP)

(72) Inventors: Takeshi Abe, Osaka (JP); Shozo Oshio, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 27 days.

This patent is subject to a terminal disclaimer.

(21) Appl. No.: 17/040,615

(22) PCT Filed: Feb. 4, 2019

(86) PCT No.: PCT/JP2019/003885
§ 371 (c)(1),
(2) Date: Sep. 23, 2020

(87) PCT Pub. No.: WO2019/187637
PCT Pub. Date: Oct. 3, 2019

(65) Prior Publication Data
US 2021/0113076 A1 Apr. 22, 2021

(30) Foreign Application Priority Data

Mar. 28, 2018 (JP) .............................. JP2018-061256
Oct. 10, 2018 (JP) .............................. JP2018-191630

(51) Int. Cl.
*A61B 1/00* (2006.01)
*A61B 1/06* (2006.01)
(Continued)

(52) U.S. Cl.
CPC ............ *A61B 1/0684* (2013.01); *A61B 1/043* (2013.01); *A61B 1/0653* (2013.01); *A61B 1/07* (2013.01); *G02B 23/2461* (2013.01)

(58) Field of Classification Search
CPC combination set(s) only.
See application file for complete search history.

(56) References Cited

U.S. PATENT DOCUMENTS 11,149,198 B2 * 10/2021 Nagao ................. H01S 5/02251
2010/0280322 A1 * 11/2010 Mizuyoshi ............ A61B 1/063
600/178

(Continued)

FOREIGN PATENT DOCUMENTS

EP 2130484 A1 12/2009
EP 2133021 A1 12/2009
(Continued)

OTHER PUBLICATIONS

Extended European Search Report dated Apr. 9, 2021, for related European Patent Application No. 19774822.1.
(Continued)

*Primary Examiner* — Timothy J Neal
(74) *Attorney, Agent, or Firm* — Renner, Otto, Boisselle & Sklar, LLP

(57) ABSTRACT

An endoscope light emitting device (1) is a light emitting device for use in a fluorescence imaging method. The endoscope light emitting device includes: a solid-state light emitting element (2); and a wavelength converter (3) including a first phosphor (4) that emits first wavelength-converted light (7), wherein the first wavelength-converted light has a light component across at least a whole of a wavelength range of 700 nm or more and 800 nm or less. An endoscope (11) includes the endoscope light emitting device. A fluorescence imaging method is a method using the endoscope light emitting device or the endoscope, and includes the (Continued)

steps of: administering a fluorescent drug to a subject; and applying the first wavelength-converted light (7) to the subject with whom the fluorescent drug has made contact.

11 Claims, 10 Drawing Sheets

(51) Int. Cl.
    *A61B 1/04*     (2006.01)
    *A61B 1/07*     (2006.01)
    *G02B 23/24*     (2006.01)

(56) References Cited

U.S. PATENT DOCUMENTS

2017/0209050 A1*   7/2017   Fengler ................ H04N 9/0455
2018/0216002 A1    8/2018   Nagao et al.

FOREIGN PATENT DOCUMENTS

| | | |
|---|---|---|
| EP | 2 356 702 B1 | 11/2017 |
| JP | 2012-152460 A | 8/2012 |
| JP | 6812461 B2 | 11/2015 |
| JP | 2016-121226 A | 7/2016 |
| JP | 2018-041856 A | 3/2018 |
| WO | 2012/069542 A1 | 5/2012 |
| WO | 2018008283 A1 | 1/2018 |

OTHER PUBLICATIONS

International Search Report for corresponding Application No. PCT/JP2019/003885, dated Mar. 26, 2019.
Written Opinion for corresponding Application No. PCT/JP2019/003885, dated Mar. 26, 2019.
Official Action for corresponding European Patent Application No. 19774822.1, dated Feb. 8, 2022.

* cited by examiner

ENDOSCOPE LIGHT EMITTING DEVICE, ENDOSCOPE USING SAME, AND FLUORESCENCE IMAGING METHOD

TECHNICAL FIELD

The present invention relates to an endoscope light emitting device, an endoscope using the light emitting device, and a fluorescence imaging method.

BACKGROUND ART

Heretofore, there has been known a method of inspecting whether or not a tumor is present in a biological tissue by using optical characteristics of the biological tissue, for Example, absorption, scattering, and the like. In Patent Literature 1, there is disclosed a biological tissue inspection device including: a light source that irradiates an inspection area of a biological tissue and emits incoherent light; and a light detector that detects reflected light or transmitted light. In general, such an inspection device is called an optical coherence tomography device, and such a method is called an optical coherence tomography method.

Meanwhile, as such a technique of inspecting whether or not a tumor is present in a biological tissue and identifying a position of the tumor, a technique called a fluorescence imaging method is also known. In the fluorescence imaging method, a fluorescent drug is administered to a subject and specifically accumulated on a tumor or the like in the subject, and thereafter, the fluorescent drug is excited by light with a specific wavelength, and fluorescence radiated from the fluorescent drug is captured and displayed as a monitor image. As described above, the fluorescence emitted from the subject is detected, thus making it possible to grasp whether or not a tumor is present and a position of the tumor. Moreover, in the fluorescence imaging method, the fluorescence radiated from such a tumor portion is detected, and accordingly, a tumor or the like can be detected more accurately than in the optical coherence tomography method.

In recent years, the fluorescence imaging method as described above has attracted attention in the field of endoscope medical care, and particularly, an indocyanine green (ICG) fluorescence method using indocyanine green as a fluorescent drug has attracted attention. The ICG is excited by near-infrared light (for Example, with a peak wavelength of 770 nm) easy to penetrate a living body, and radiates near-infrared light (for Example, with a fluorescence peak wavelength of 810 nm) longer in wavelength than this excitation near-infrared light. Therefore, the fluorescence emitted from the ICG is detected, thus making it possible to observe and cure a tumor and a lymph node under a mucosa. Note that light within a wavelength range of 650 nm or more and less than 1400 nm is difficult to be scattered by hemoglobin and water in a living body, and accordingly, is easy to penetrate the living body. This wavelength range is generally called an in-vivo window.

As an endoscope using the ICG fluorescence method, there is known an endoscope using a light emitting device provided with, as an excitation source of the ICG, a laser element that emits near-infrared light with a central wavelength of 780 nm (see Patent Literature 2).

CITATION LIST

Patent Literature

Patent Literature 1: Japanese Patent No. 5812461
Patent Literature 2: Japanese Unexamined Patent Application Publication No. 2012-152460

SUMMARY OF INVENTION

However, when such a laser element as in Patent Literature 2 is used as an excitation source of the ICG, there are two problems as below. One of the problems is: since a full width at half maximum of a light emission spectrum of the near-infrared light emitted by the laser element is narrow, the ICG has not sometimes been sufficiently excited by the near-infrared light emitted by the laser element when excitation characteristics of the ICG change due to variation of characteristics. The other problem is: the laser element that emits the near-infrared light has not been able to sufficiently excite the ICG since an output thereof in the wavelength range in which it is easy to excite the ICG is low.

The present invention has been made in consideration of such problems as described above, which are inherent in the prior art. It is an object of the present invention to provide an endoscope light emitting device capable of efficiently exciting the fluorescent drug even if the variation of characteristics occurs and radiating high-output near-infrared light, an endoscope using the light emitting device, and a fluorescence imaging method.

In order to solve the above-described problems, an endoscope light emitting device according to a first aspect of the present invention is an endoscope light emitting device for use in a fluorescence imaging method. The endoscope light emitting device includes: a solid-state light emitting element; and a wavelength converter including a first phosphor that emits first wavelength-converted light, wherein the first wavelength-converted light has a light component across at least a whole of a wavelength range of 700 nm or more and 800 nm or less.

An endoscope according to a second aspect of the present invention includes the endoscope light emitting device according to the first aspect.

A fluorescence imaging method according to a third aspect of the present invention is a method using the endoscope light emitting device according to the first aspect or the endoscope according to the second aspect. The fluorescence imaging method includes the steps of: administering a fluorescent drug to a subject; and applying the first wavelength-converted light to the subject with whom the fluorescent drug has made contact.

DESCRIPTION OF EMBODIMENTS

Figure 1:
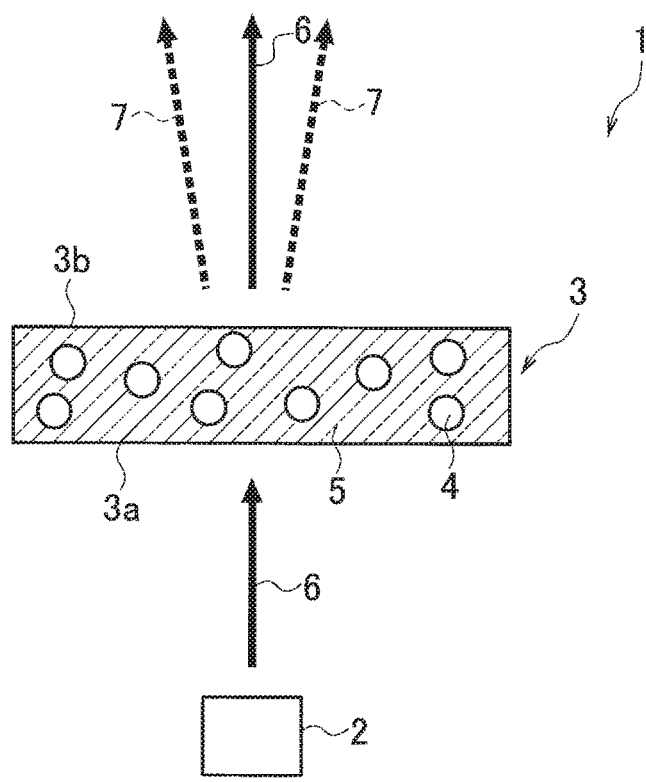
FIG. 1 is a schematic cross-sectional view illustrating an Example of a light emitting device according to this embodiment.

Referring to the drawings, a description will be given below of an endoscope light emitting device according to this embodiment, an endoscope using the light emitting device, and a fluorescence imaging method. Note that dimensional ratios in the drawings are exaggerated for convenience of explanation, and are sometimes different from actual ratios.

[Endoscope Light Emitting Device]

As illustrated in FIG. 1 to FIG. 4, each of endoscope light emitting devices 1, 1A, 1B and 1C according to this embodiment includes at least a solid-state light emitting element 2 and a wavelength converter 3 or 3A including a first phosphor 4 that emits first wavelength-converted light 7. Each of the endoscope light emitting devices 1, 1A, 1B and 1C is a device in which the wavelength converter 3 or 3A radiates fluorescence when primary light 6 radiated from the solid-state light emitting element 2 enters the wavelength converter 3 or 3A. Note that, in this description, "endoscope light emitting device" will be also referred to as "light emitting device".

The solid-state light emitting element 2 is a light emitting element that radiates the primary light 6. As such a solid-state light emitting element 2, for Example, a laser element such as a surface-emitting laser diode is used. Then, for Example, output energy of laser light radiated by the laser element is preferably 0.2 W or more, more preferably 1 W or more, still more preferably 5 W or more. Moreover, for Example, an energy density of the laser light is preferably 0.5 W/mm² or more, more preferably 2 W/mm² or more, still more preferably 10 W/mm² or more. Thus, a phosphor in each of the wavelength converters 3 and 3A can be excited by the high-output laser light, and accordingly, the light emitting device becomes capable of radiating high-output near-infrared light. Note that an upper limit of the output energy of the laser light radiated by the laser element is not particularly limited; however, can be set to 20 W for Example. An upper limit of the energy density of the laser light is not particularly limited, either; however, can be set to 50 W/mm² for Example.

It is preferable that the solid-state light emitting element 2 radiate laser light having a maximum intensity value within a wavelength range of 430 nm or more and 480 nm or less. Moreover, it is preferable that the solid-state light emitting element 2 include a blue laser element as an excitation source to radiate blue laser light. Thus, the phosphor in each of the wavelength converters 3 and 3A can be excited with high efficiency, and accordingly, the light emitting device becomes capable of radiating the high-output near-infrared light.

The solid-state light emitting element 2 may be an element that radiates laser light having a maximum intensity value within a wavelength range of 500 nm or more and 560 nm or less. Thus, the phosphor in each of the wavelength converters 3 and 3A can be excited by the high-output laser light, and accordingly, the light emitting device becomes capable of radiating the high-output near-infrared light.

Moreover, the solid-state light emitting element 2 may be an element that radiates laser light having a maximum intensity value within a wavelength range of 600 nm or more and 700 nm or less. Thus, it becomes possible to excite the phosphor in each of the wavelength converters 3 and 3A by red-series light with relatively low energy, and accordingly, a light emitting device can be obtained, which emits high-output near-infrared light, and in which heat generation due to a Stoke's loss of the phosphor is a little.

Types of the solid-state light emitting element 2 provided in each of the endoscope light emitting devices 1, 1A, 1B and 1C are not particularly limited. However, the number of types of the solid-state light emitting element 2 provided in each of the endoscope light emitting devices 1, 1A, 1B and 1C is preferably three or less, more preferably two or less, still more preferably one. With such a configuration, a simple configuration in which the number of types of the solid-state light emitting element 2 is small is obtained, and accordingly, compact endoscope light emitting devices 1, 1A, 1B and 1C can be obtained.

Note that each of the light emitting devices 1, 1A, 1B and 1C may further include a laser element that does not excite the wavelength converter 3 or 3A. Thus, a light emitting device can be obtained, which is oriented for a medical device that can combine the fluorescence imaging method using the near-infrared light emitted by each of the wavelength converters 3 and 3A and another treatment using laser light emitted by a laser element that does not excite each of the wavelength converters 3 and 3A with each other. Note that such another treatment using the laser light emitted by the laser element includes a treatment using an optical coherence tomography method, a treatment using a photodynamic therapy, a treatment using narrow band imaging (NBI), a laser knife treatment, and the like.

Figure 2:
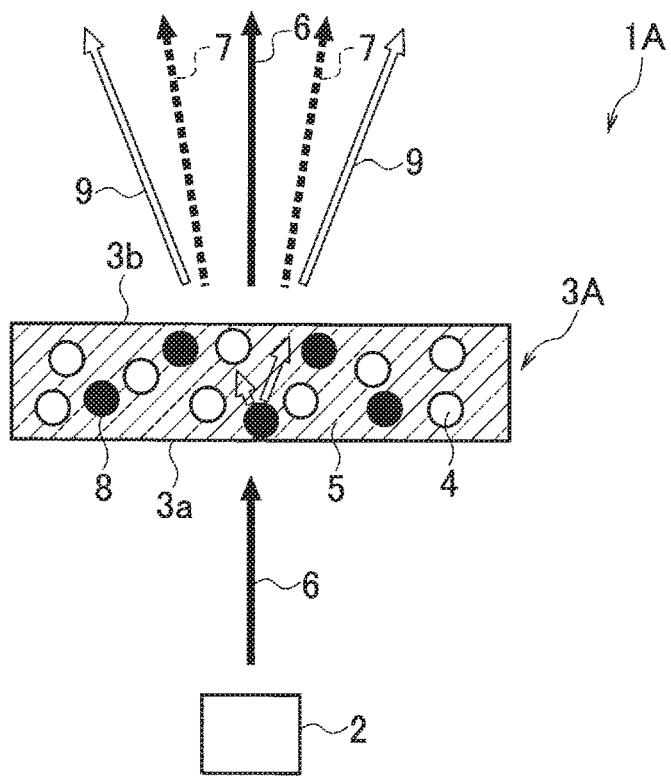
FIG. 2 is a schematic cross-sectional view illustrating another Example of the light emitting device according to this embodiment.
Figure 3:
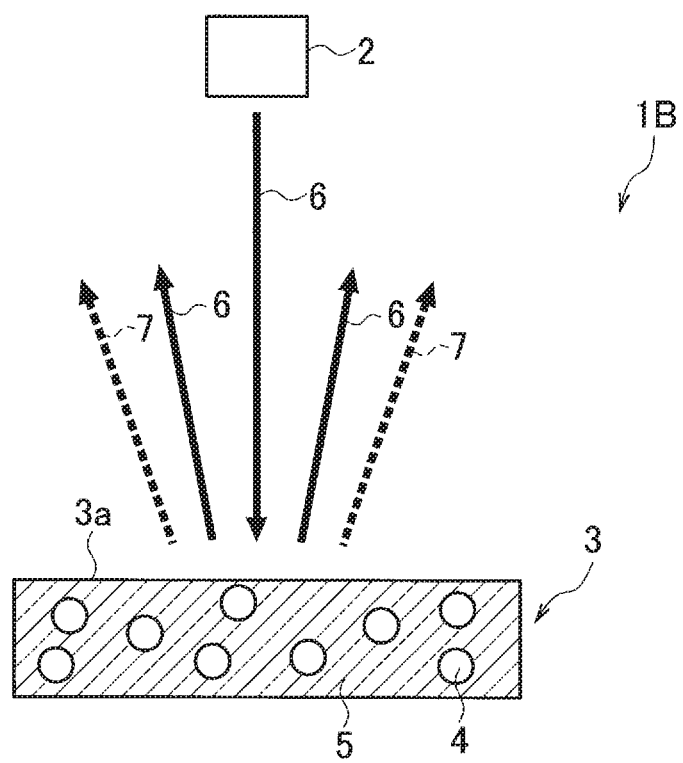
FIG. 3 is a schematic cross-sectional view illustrating still another Example of the light emitting device according to this embodiment.
Figure 4:
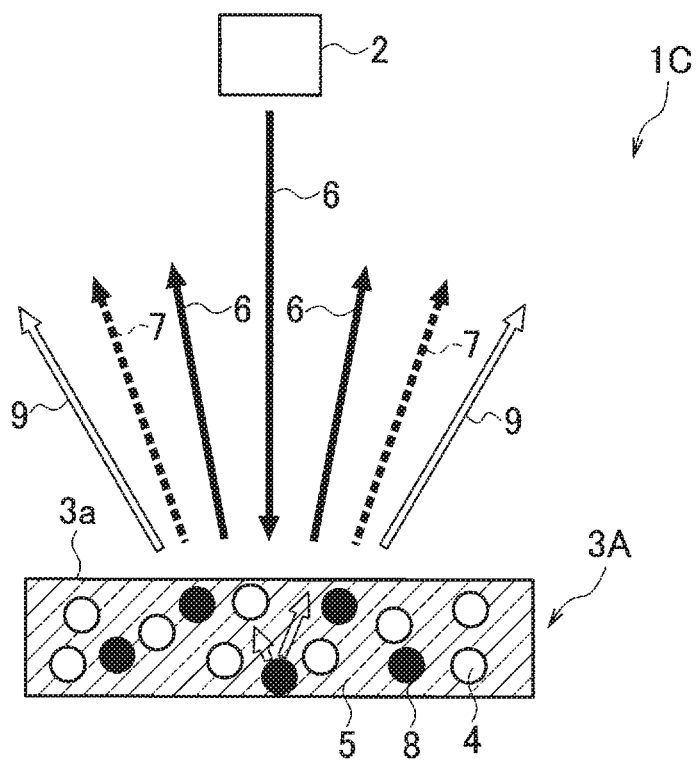
FIG. 4 is a schematic cross-sectional view illustrating yet another Example of the light emitting device according to this embodiment.

As illustrated in FIG. 1 to FIG. 4, the wavelength converter 3 or 3A receives the primary light 6, thereby radiating fluorescence having a longer wavelength than the primary light 6. Each of the wavelength converters 3 and 3A illustrated in FIG. 1 and FIG. 2 is configured to receive the primary light 6 by a front surface 3a and radiate the fluorescence from a back surface 3b. In contrast, each of the wavelength converters 3 and 3A illustrated in FIG. 3 and FIG. 4 is configured to receive the primary light 6 on a front surface 3a and radiate the fluorescence on the same front surface 3a.

Each of the wavelength converters 3 and 3A includes the first phosphor 4 that receives the primary light 6 and emits the first wavelength-converted light 7, and the first wavelength-converted light 7 is light having a light component across at least the whole of a wavelength range of 700 nm or more and 800 nm or less. Therefore, each of the light emitting devices 1, 1A, 1B and 1C can emit continuous spectrum light having a light component in a wavelength range of at least 700 nm or more and 800 nm or less.

The first phosphor 4 included in each of the wavelength converters 3 and 3A is not particularly limited as long as the first wavelength-converted light 7 has a light component across at least the whole of such a wavelength range of 700 nm or more and 800 nm or less. However, preferably, the first phosphor 4 includes at least one of a $Eu^{2+}$-activated phosphor and a $Ce^{3+}$-activated phosphor. $Ce^{3+}$ and $Eu^{2+}$ take the mechanism of light absorption and emission, which are based on $4f_n \leftrightarrow 4f_{n-1}5d_1$ allowed transition. Therefore, wavelengths of the absorption and the light emission are changed depending on host crystals in which these are activated. Hence, $Ce^{3+}$ or $Eu^{2+}$ is taken as a light emission center, and appropriate host crystals are selected, thus making it possible to obtain a fluorescent component that forms a smooth band spectrum in at least the wavelength range of 700 nm or more and 800 nm or less. Note that, in the above-mentioned $4f_n \leftrightarrow 4f_{n-1}5d_1$ allowed transition, $Ce^{3+}$ applies to n=1, and $Eu^{2+}$ applies to n=7.

It is preferable that the first phosphor 4 include at least a $Cr^{3+}$-activated phosphor. $Cr^{3+}$ takes the mechanism of light absorption and emission, which are based on d-d transition. Therefore, wavelengths of the absorption and the light emission are changed depending on host crystals in which $Cr^{3+}$ is activated. Hence, $Cr^{3+}$ is taken as a light emission center, and appropriate host crystals are selected, thus making it possible to obtain a fluorescent component that forms a smooth band spectrum in at least the wavelength range of 700 nm or more and 800 nm or less.

Preferably, the first phosphor 4 is an oxide-based phosphor, more preferably, an oxide phosphor. Note that the oxide-based phosphor refers to a phosphor that contains oxygen but does not contain nitrogen, and for Example, there can be mentioned alkaline earth metal oxide, alkaline earth metal halo-aluminate, and rare earth aluminate, each of which has a calcium ferrite-type structure.

Oxides are stable substances in the atmosphere, and accordingly, even when the oxide phosphors generate heat due to high-density photoexcitation by laser light, such a quality degradation of phosphor crystals as caused in nitride phosphors, which may be caused by oxidation in the atmosphere, is less likely to occur. Therefore, when all of the phosphors included in each of the wavelength converters 3 and 3A are such oxide phosphors, a light emitting device with high reliability can be obtained.

Preferably, the first phosphor 4 is a nitride-based phosphor, more preferably, a nitride phosphor. Moreover, preferably, the first phosphor 4 is an oxynitride-based phosphor, more preferably, an oxynitride phosphor. Nitrides have intense covalent bonding properties, and can take a variety of modified Examples in terms of composition, and accordingly, can also easily control a fluorescent color and improve temperature quenching. Moreover, nitrides are also excellent in thermal conductivity, and accordingly, are also advantageous in miniaturization of the light emitting device. Therefore, when all of the phosphors included in each of the wavelength converters 3 and 3A are the nitride-based phosphors, color tone control of the light emitted by the light emitting device becomes easy, and it also becomes easy to design a small device.

It is also preferable that the first phosphor 4 have a crystal structure of garnet. Moreover, it is also preferable that the first phosphor 4 be an oxide phosphor having the crystal structure of garnet. Phosphors having such a garnet structure, and particularly oxides having the same have a polyhedral particle shape close to a sphere, and are excellent in dispersibility for a group of phosphor particles. Therefore, when the phosphor included in each of the wavelength converters 3 and 3A has a garnet structure, then a wavelength converter excellent in light transparency becomes relatively easily producible, and it becomes possible to increase the output of the light emitting device. Moreover, since the phosphors having the crystal structure of garnet have been actually used as phosphors for LED, such a highly reliable light emitting device can be obtained in such a manner that the first phosphor 4 has the crystal structure of garnet.

It is preferable that the first phosphor 4 be a phosphor containing, as a main component, at least one selected from the group consisting of rare earth silicate, rare earth aluminate, rare earth aluminosilicate, alkaline earth metal aluminonitride silicate, and rare earth nitride silicate. Alternatively, it is preferable that the first phosphor 4 be a phosphor composed based on at least one selected from the group consisting of rare earth silicate, rare earth aluminate, rare earth aluminosilicate, alkaline earth metal aluminonitride silicate, and rare earth nitride silicate. Such a first phosphor 4 as described above is used, whereby a part of the primary light 6 becomes easily convertible into near-infrared light. Therefore, it becomes possible to obtain near-infrared light in which a full width at half maximum of a fluorescence spectrum is large.

Specifically, it is preferable that the first phosphor 4 be a phosphor composed based on a compound (A) containing as a main component, at least one selected from the group consisting of $RE_2MMg(SiO_4)_3$, $RE_3Al_2(AlO_4)_3$, $RE_3Mg_2(SiO_4)_2(AlO_4)$, $MRE_2O_4$, $MAlSiN_3$, and $RE_3Si_6N_{11}$. Alternatively, it is preferable that the first phosphor 4 be a phosphor composed based on at least one selected from the group consisting of $RE_2MMg(SiO_4)_3$, $RE_3Al_2(AlO_4)_3$, $RE_3Mg_2(SiO_4)_2(AlO_4)$, $MRE_2O_4$, $MAlSiN_3$, and $RE_3Si_6N_{11}$. Alternatively, it is preferable that the first phosphor 4 be a phosphor composed based on a solid solution containing the compound (A) as an end member. Note that M is alkaline earth metal, and RE is a rare earth element.

It is preferable that the first phosphor 4 be composed of ceramics. Thus, heat dissipation of the first phosphor 4 increases, and accordingly, a decrease of the output of the first phosphor 4 due to temperature quenching is suppressed, and a light emitting device that emits the high-output near-infrared light can be obtained.

As mentioned above, in each of the light emitting devices 1, 1A, 1B and 1C, the first wavelength-converted light 7 emitted by the first phosphor 4 is light having a light component across at least the whole of the wavelength range of 700 nm or more and 800 nm or less. Thus, a fluorescent drug can be efficiently excited. However, it is more preferable that the first wavelength-converted light 7 have a light component across at least the whole of a wavelength range of 750 nm or more and 800 nm or less. Moreover, it is also preferable that the first wavelength-converted light 7 have a light component across the whole of a wavelength range of 600 nm or more and 800 nm or less. Furthermore, preferably, the first wavelength-converted light 7 emitted by the first phosphor 4 has a fluorescence peak within the wavelength range of 600 nm or more and 800 nm or less, more preferably, has a fluorescence peak within the wavelength range of 700 nm or more and 800 nm or less. Thus, a configuration is formed, in which a fluorescent drug can more efficiently absorb the light component in the near-infrared range, which is emitted by the first phosphor 4. Therefore, an endoscope light emitting device can be provided, which is capable of increasing a light quantity of the near-infrared light radiated from the fluorescent drug.

In the first wavelength-converted light 7 emitted by the first phosphor 4, a 1/e fluorescence lifetime is preferably 20 ns or more and 1000 µs or less, more preferably 20 ns or more and 100 µs or less. Moreover, in the first wavelength-converted light 7, the 1/e fluorescence lifetime is still more preferably 20 ns or more and 2000 ns or less, particularly preferably 20 ns or more and 100 ns or less. Thus, even when alight density of excitation light that excites the first phosphor 4 is high, an output of such fluorescence emitted by the first phosphor 4 becomes less likely to saturate. Therefore, an endoscope light emitting device capable of emitting the high-output near-infrared light can be obtained.

Energy (radiant flux of fluorescence) of the first wavelength-converted light 7 emitted by the first phosphor 4 is preferably 0.1 W or more, more preferably 0.3 W or more, still more preferably 1 W or more. Thus, it becomes possible to excite the fluorescent drug by the high-output near-infrared light, and accordingly, an endoscope light emitting device is formed, which is capable of increasing the light quantity of the near-infrared light radiated from the fluorescent drug. Moreover, thus, a penetration depth of the near-infrared light with respect to a living body increases, and therefore, an endoscope light emitting device is formed, which is capable of exciting even a fluorescent drug present in the depth of the living body. Note that an upper limit of the energy of the first wavelength-converted light 7 emitted by the first phosphor 4 is not particularly limited; however, can be set to 3 W for Example.

As illustrated in FIG. 1, it is preferable that the wavelength converter 3 further include a sealing material 5, which disperses the first phosphor 4, in addition to the first phosphor 4. Then, in the wavelength converter 3, it is preferable that the first phosphor 4 be dispersed in the sealing material 5. The first phosphor 4 is dispersed in the sealing material 5, whereby it becomes possible to efficiently absorb the primary light 6 emitted by the solid-state light emitting element 2, and to perform wavelength conversion for the primary light 6 into the near-infrared light. Moreover, it can be made easy to mold the wavelength converter 3 into a sheet shape or a film shape.

Preferably, the sealing material 5 is at least one of an organic material and an inorganic material, and particularly, at least one of a transparent (translucent) organic material and a transparent (translucent) inorganic material. As such a sealing material made of the organic material, for Example, a transparent organic material such as a silicone resin is mentioned. As such a sealing material made of the inorganic material, for Example, a transparent inorganic material such as low-melting-point glass is mentioned.

As illustrated in FIG. 1 and FIG. 3, the wavelength converter 3 includes the first phosphor 4 that emits the first wavelength-converted light 7. However, it is preferable that, as illustrated in FIG. 2 and FIG. 4, the wavelength converter further include a second phosphor 8 that absorbs the primary light 6 emitted by the solid-state light emitting element 2 and emits second wavelength-converted light 9 that is visible light. The wavelength converter 3A includes the second phosphor 8, thus making it possible to radiate white output light by additive color mixture of the second wavelength-converted light 9 with the primary light 6 emitted by the solid-state light emitting element 2, for Example, with blue laser light.

The second phosphor 8 included in the wavelength converter 3A is not particularly limited as long as being capable of absorbing the primary light 6 emitted by the solid-state light emitting element 2 and radiating the second wavelength-converted light 9 that is visible light. It is preferable that the second phosphor 8 be a $Ce^{3+}$-activated phosphor composed based on a compound containing, as a main component, at least one selected from the group of compounds consisting of a garnet-type crystal structure, a calcium ferrite-type crystal structure, and a lanthanum silicon nitride ($La_3Si_6N_{11}$)-type crystal structure. Alternatively, it is preferable that the second phosphor 8 be a $Ce^{3+}$-activated phosphor composed based on at least one compound selected from the group of compounds consisting of a garnet-type crystal structure, a calcium ferrite-type crystal structure, and a lanthanum silicon nitride ($La_3Si_6N_{11}$)-type crystal structure. Such a second phosphor 8 as described above is used, whereby output light that has a large quantity of green to yellow-series light components becomes obtainable.

Specifically, it is preferable that the second phosphor 8 be a $Ce^{3+}$-activated phosphor composed based on a compound (B) containing, as a main component, at least one selected from the group consisting of $M_3RE_2(SiO_4)_3$, $RE_3Al_2(AlO_4)_3$, $MRE_2O_4$, and $RE_3Si_6N_{11}$. Alternatively, it is preferable that the second phosphor 8 be a $Ce^{3+}$-activated phosphor composed based on at least one selected from the group consisting of $M_3RE_2(SiO_4)_3$, $RE_3Al_2(AlO_4)_3$, $MRE_2O_4$, and $RE_3Si_6N_{11}$. Alternatively, it is preferable that the second phosphor 8 be a $Ce^{3+}$-activated phosphor composed based on a solid solution containing the compound (B) as an end member. Note that M is alkaline earth metal, and RE is a rare earth element.

Such a second phosphor 8 as described above absorbs light within the wavelength range of 430 nm or more and 480 nm or less well, and converts the absorbed light into the green to yellow-series light having the maximum intensity value within a wavelength range of 540 nm or more and 590 nm or less highly efficiently. Therefore, such a phosphor as described above is used as the second phosphor 8, whereby a visible light component becomes easily obtainable.

When the wavelength converter 3A includes the first phosphor 4 and the second phosphor 8, it is preferable that the first phosphor 4 emit the first wavelength-converted light 7 by absorbing at least either one of the primary light 6 emitted by the solid-state light emitting element 2 and the second wavelength-converted light 9 emitted by the second phosphor 8. As mentioned above, it is preferable that the first phosphor 4 be a phosphor that absorbs the primary light 6 emitted by the solid-state light emitting element 2 and emits the first wavelength-converted light 7 that is near-infrared light. However, the first phosphor 4 may be a phosphor that absorbs the second wavelength-converted light 9 emitted by the second phosphor 8 and emits the first wavelength-converted light 7 that is near-infrared light. That is, the second phosphor 8 may be excited by the primary light 6 to radiate the second wavelength-converted light 9, and the first phosphor 4 may be excited by the second wavelength-converted light 9 to radiate the first wavelength-converted light 7. In this case, even if the first phosphor 4 is a phosphor that is hardly excited by the primary light 6, interposition of the second phosphor 8 makes it possible to excite the first phosphor 4 by the fluorescence emitted by the second phosphor 8. Thus, it becomes possible to select, as the first phosphor 4, a phosphor that absorbs visible light, and accordingly, a choice of options for the first phosphor 4 is widened, and a light emitting device easy to industrially produce is formed. Moreover, when the first phosphor 4 absorbs the second wavelength-converted light 9 to emit the first wavelength-converted light 7, a light emitting device is formed, which is capable of emitting the first wavelength-converted light 7 in which a light component intensity of the near-infrared light is large.

It is preferable that each of the wavelength converters 3 and 3A be composed of an inorganic material. Herein, the inorganic material means a material other than organic materials, and is a concept involving ceramics and metals. Each of the wavelength converters 3 and 3A is made of an inorganic material, whereby thermal conductivity thereof is increased in comparison with a wavelength converter including an organic material such as a sealing resin, and accordingly, heat dissipation design can be easily prepared. Therefore, even if the phosphor is subjected to high-density photoexcitation by the primary light 6 radiated from the solid-state light emitting element 2, a temperature rise of each of the wavelength converters 3 and 3A can be suppressed effectively. As a result, temperature quenching of the phosphor in each of the wavelength converters 3 and 3A is suppressed, and it becomes possible to increase the output of the light emission.

As mentioned above, since it is preferable that each of the wavelength converters 3 and 3A be made of an inorganic material, it is preferable that the sealing material 5 be made of an inorganic material. Moreover, it is preferable to use zinc oxide (ZnO) as such an inorganic material. Thus, the heat dissipation of the phosphor further increases, and accordingly, a decrease of the output of the phosphor due to temperature quenching is suppressed, and it becomes possible to obtain a light emitting device that emits the high-output near-infrared light.

Note that the wavelength converter 3 or 3A can also be made as a wavelength converter that does not use the sealing material 5. In this case, particles of the phosphors just need to be adhered to one another by using an organic or inorganic binding agent. Moreover, the particles of the phosphors can also be adhered to one another by using a heating reaction of the phosphors. As the binding agent, there can be used a resin-based adhesive used commonly, or ceramic fine particles, low-melting-point glass or the like. The wavelength converter that does not use the sealing material 5 can be thinned in thickness, and accordingly, can be suitably used for the light emitting device.

Next, functions of the light emitting device according to this embodiment will be described. In the light emitting device 1 illustrated in FIG. 1, first, the primary light 6 (laser light) radiated from the solid-state light emitting element 2 is applied to the front surface 3a of the wavelength converter 3. The applied primary light 6 penetrates the wavelength converter 3. Then, when the primary light 6 penetrates the wavelength converter 3, the first phosphor 4 included in the wavelength converter 3 absorbs a part of the primary light 6 and radiates the first wavelength-converted light 7. As described above, light including the primary light 6 and the first wavelength-converted light 7 is radiated as output light from the back surface 3b of the wavelength converter 3.

In the light emitting device 1A illustrated in FIG. 2, first, the primary light 6 (laser light) radiated from the solid-state light emitting element 2 is applied to the front surface 3a of the wavelength converter 3A. The applied primary light 6 penetrates the wavelength converter 3A. Then, when the primary light 6 penetrates the wavelength converter 3A, the second phosphor 8 included in the wavelength converter 3A absorbs a part of the primary light 6 and radiates the second wavelength-converted light 9. Moreover, the first phosphor 4 included in the wavelength converter 3A absorbs a part of the primary light 6 and/or the second wavelength-converted light 9 and radiates the first wavelength-converted light 7. As described above, light including the primary light 6, the first wavelength-converted light 7, and the second wavelength-converted light 9 is radiated as output light from the back surface 3b of the wavelength converter 3A.

In the light emitting device 1B illustrated in FIG. 3, first, the primary light 6 (laser light) radiated from the solid-state light emitting element 2 is applied to the front surface 3a of the wavelength converter 3. Much of the primary light 6 enters the inside of the wavelength converter 3 from the front surface 3a of the wavelength converter 3, and the rest thereof is reflected on the front surface 3a. In the wavelength converter 3, the first wavelength-converted light 7 is radiated from the first phosphor 4 excited by the primary light 6, and the first wavelength-converted light 7 is radiated from the front surface 3a.

In the light emitting device 1C illustrated in FIG. 4, first, the primary light 6 (laser light) radiated from the solid-state light emitting element 2 is applied to the front surface 3a of the wavelength converter 3A. Much of the primary light 6 enters the inside of the wavelength converter 3A from the front surface 3a of the wavelength converter 3A, and the rest thereof is reflected on the front surface 3a. In the wavelength converter 3A, the second wavelength-converted light 9 is radiated from the second phosphor 8 excited by the primary light 6, and the first wavelength-converted light 7 is radiated from the first phosphor 4 excited by the primary light 6 and/or the second wavelength-converted light 9. Then, the first wavelength-converted light 7 and the second wavelength-converted light 9 are radiated from the front surface 3a.

As described above, the light emitting device of this embodiment radiates the first wavelength-converted light 7 having a light component across at least the whole of the wavelength range of 700 nm or more and 800 nm or less, and accordingly, by the first wavelength-converted light 7, can efficiently excite the ICG as a fluorescent drug administered to the subject.

Figure 5:
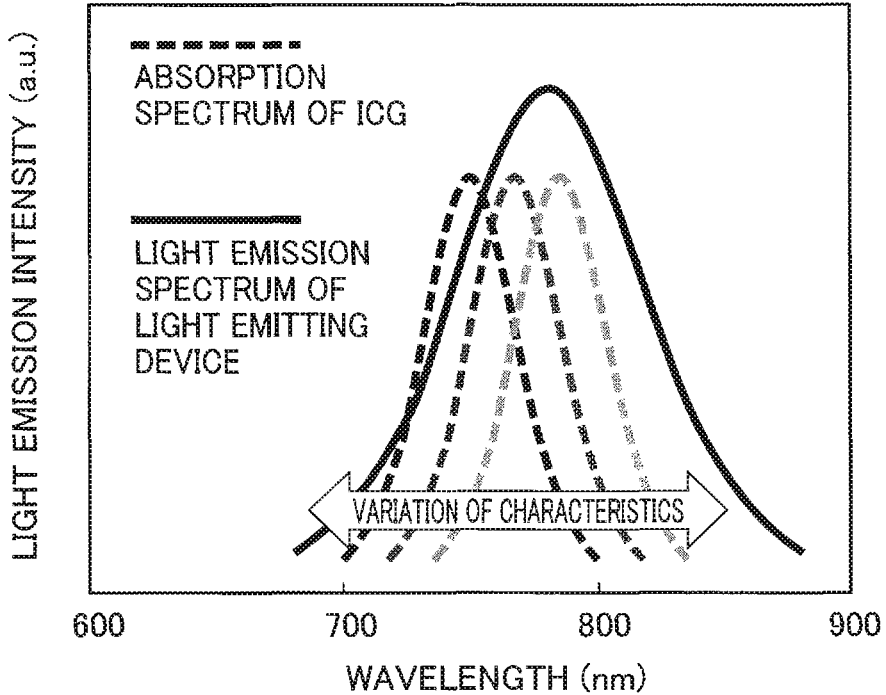
FIG. 5 is a graph abstractly illustrating a relationship between a light emission spectrum of the light emitting device according to this embodiment and an absorption spectrum of indocyanine green.
Figure 6:
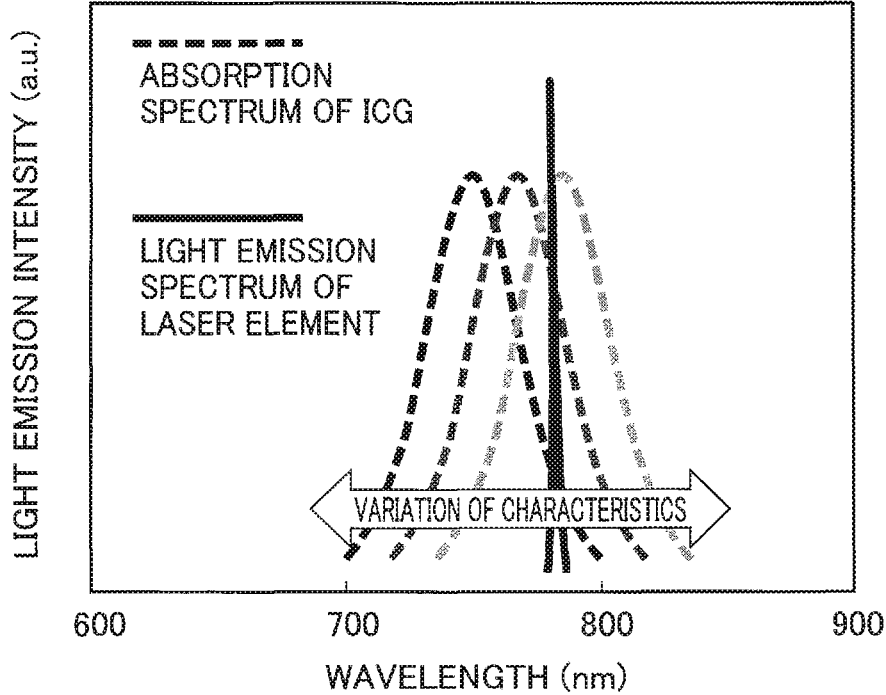
FIG. 6 is a graph abstractly illustrating a relationship between a light emission spectrum of a laser element that emits near-infrared light and an absorption spectrum of the indocyanine green.

Here, FIG. 5 illustrates a concept of a relationship between a light emission spectrum of the light emitting device according to this embodiment and an absorption spectrum of the indocyanine green. Moreover, FIG. 6 illustrates a concept of a relationship between a light emission spectrum of a laser element that emits near-infrared light and an absorption spectrum of the indocyanine green. In the indocyanine green (ICG) that is a fluorescent drug, absorption characteristics thereof sometimes change due to a difference in the internal environment of the subject, differences in types of a functional group, a substituent group, and side chains, which are introduced in order to be accumulated into a region (affected area) of a tumor, and the like. Moreover, the absorption characteristics of the ICG sometimes vary due to differences in production lot and production condition. That is, as illustrated in FIG. 5, a peak wavelength of the absorption spectrum of the ICG changes to some extent due to influences of these. However, the light emitting device continuously emits the light component across at least the whole of the wavelength range of 700 nm or more and 800 nm or less, and accordingly, even if the absorption characteristics of the ICG change, the absorption spectrum of the ICG and the light emission spectrum of the first wavelength-converted light 7 overlap each other to a large extent. Therefore, the ICG efficiently absorbs the first wavelength-converted light 7, and accordingly, for Example, the ICG can radiate long-wavelength near-infrared light with a fluorescence peak wavelength of 810 nm at a high intensity. As a result, it becomes possible to easily specify an accumulated region of the ICG in the subject.

In contrast, when the laser element that emits near-infrared light is used as in Patent Literature 2, a full width at half maximum of a light emission spectrum of the near-infrared light becomes extremely narrow in terms of the characteristics of the laser element. Therefore, when the absorption characteristics of the ICG change as illustrated in FIG. 6, such an overlap between the absorption spectrum of the ICG and the light emission spectrum of the near-infrared light becomes small, and therefore, the ICG becomes less likely to be excited. As a result, there is a possibility that an intensity of the fluorescence emitted from the ICG becomes small to make it difficult to specify the accumulated region of the ICG in the subject.

Note that, in an organic fluorescent drug, absorption characteristics and light emission characteristics thereof sometimes change due to the solvatochromic effect (effect of changing a ground state and an excited state by a change of a solvent polarity), the differences in types of the functional group, the substituent group, and the side chains, and the like. Moreover, in the organic fluorescent drug, the absorption characteristics and light emission characteristics thereof sometimes change also due to a change of electron withdrawing characteristics, which is caused by molecular association (coupling of the same types of molecules by intermolecular force), and the like. Therefore, the light emitting device according to this embodiment can be suitably used also for a fluorescence imaging method using a fluorescent drug other than the ICG, in which an excitation spectrum and a light emission spectrum are present in the near-infrared light region.

In the light emitting device of this embodiment, it is preferable that the wavelength converter further include the second phosphor 8, which emits the second wavelength-converted light 9 that is visible light, in addition to the first phosphor 4 that emits the first wavelength-converted light 7. Thus, it becomes possible to apply the second wavelength-converted light 9 to a surface of a body tissue, and to observe a state of the surface of the body tissue.

As described above, each of the endoscope light emitting devices 1, 1A, 1B and 1C of this embodiment is a light emitting device for use in the fluorescence imaging method, and includes the solid-state light emitting element 2, and the wavelength converter 3 or 3A including the first phosphor 4 that emits the first wavelength-converted light 7. Moreover, the first wavelength-converted light 7 has a light component across at least the whole of the wavelength range of 700 nm or more and 800 nm or less. Then, the fluorescent drug accumulated on the subject is excited by the first wavelength-converted light 7, and radiates fluorescence with a longer wavelength than that of the first wavelength-converted light 7.

Each of the light emitting devices 1, 1A, 1B and 1C radiates light having a light component across at least the whole of the wavelength range of 700 nm or more and 800 nm or less, and accordingly, becomes capable of exciting the fluorescent drug with high efficiency even when the fluorescent drug varies in characteristics. Moreover, when the solid-state light emitting element 2 radiates the laser light, an intensity of the first wavelength-converted light 7 emitted from the first phosphor 4 becomes high. Therefore, it becomes possible to excite the fluorescent drug in the subject with higher efficiency, and to radiate the long-wavelength fluorescence.

Note that the primary light 6 radiated from the solid-state light emitting element 2 may be included in the output light of each of the light emitting devices 1, 1A, 1B and 1C. In such a way, such a light emitting device can be obtained, which is oriented for a medical device that can combine the fluorescence imaging method and another treatment with each other by using the primary light 6 different in wavelength from the first wavelength-converted light 7. Another treatment includes, for Example, a treatment using narrow band imaging. Moreover, the primary light 6 does not have to be included in the output light of each of the light emitting devices 1, 1A, 1B and 1C. In such a way, only the first wavelength-converted light 7 becomes the output light, and a light emitting device can be obtained, which has a small amount of noise component and is suitable for the fluorescence imaging method.

It is preferable that the solid-state light emitting element 2 be a blue laser element that radiates laser light having the maximum intensity value within the wavelength range of 430 nm or more and 480 nm or less. The blue laser element has a higher output than the laser element that is used in Patent Literature 2 and emits near-infrared light. Therefore, the blue laser element and each of the wavelength converters 3 and 3A are combined with each other, whereby near-infrared light with a higher output than heretofore can be radiated, and it becomes possible to excite the fluorescent drug in the subject with high efficiency.

Note that, in each of the endoscope light emitting devices 1A and 1C of this embodiment, it is more preferable that the peak of the fluorescence emitted by the second phosphor 8 stay within a wavelength range of 500 nm or more and 700 nm or less, and that the solid-state light emitting element 2 include the blue laser element as an excitation source. Thus, the light emitting device can radiate a white light component by the additive color mixture of the second wavelength-converted light 9 emitted by the second phosphor 8 and the blue light component emitted by the solid-state light emitting element 2. Therefore, it becomes possible to apply the white light component to the surface of the body tissue, and to observe the state of the surface of the body tissue. Moreover, the phosphor that has been actually used highly often can be used as the second phosphor 8, and further, as the solid-state light emitting element 2, a blue semiconductor laser element can be used, which is easily available from the market, is relatively inexpensive, and has been actually used highly often. Therefore, it becomes possible to easily obtain the endoscope light emitting device suitable for industrial production.

Each of the light emitting devices 1, 1A, 1B and 1C of this embodiment can be used also for a fluorescence imaging method using a fluorescent drug other than the ICG, in which an excitation spectrum and a light emission spectrum are present in the near-infrared light region (for Example, a wavelength range of 650 nm or more and less than 1400 nm). Such a fluorescent drug includes, for Example, a phthalocyanine-based compound, a talaporfin sodium-based compound, a dipicolylcyanine (DIPCY)-based compound, and the like.

[Endoscope and Endoscope System]

Next, Examples of an endoscope according to tis embodiment and an endoscope system using the endoscope will be described with reference to FIG. 7 and FIG. 8. Note that the endoscope which will be described below is an Example of including the light emitting device 1A or 1C that radiates visible light in addition to near-infrared light.
(Endoscope)

The endoscope according to this embodiment includes the above-mentioned endoscope light emitting device. As illustrated in FIG. 7, the endoscope 11 includes a scope 110, a light source connector 111, a mount adapter 112, a relay lens 113, a camera head 114, and an operation switch 115.

The scope 110 is an elongated light guide member capable of guiding light from a terminal end thereof to a distal end thereof, and is inserted into a body at the time of use. The scope 110 includes an imaging window 110z on a distal end thereof, and an optical material such as optical glass and optical plastics is used for the imaging window 110z. The scope 110 further includes an optical fiber that guides, to the distal end, light introduced from the light source connector 111, and an optical fiber through which an optical image incident from the imaging window 110z is to be transmitted.

The mount adapter 112 is a member for attaching the scope 110 to the camera head 114. A variety of the scopes 110 are freely detachably attached to the mount adapter 112.

From the light emitting device 1A or 1C, the light source connector 111 introduces illumination light to be applied to the affected area and the like in the body. In this embodiment, the illumination light includes visible light and near-infrared light. The light introduced into the light source connector 111 is introduced via the optical fiber to the distal end of the scope 110, and is applied from the imaging window 110z to the affected area and the like in the body. Note that, as illustrated in FIG. 7, a transmission cable 111z for guiding the illumination light from the light emitting device 1A or 1C to the scope 110 is connected to the light source connector 111. The transmission cable 111z includes the optical fiber.

The relay lens 113 converges an optical image, which is to be transferred through the scope 110, onto an imaging surface of an image sensor. Note that the relay lens 113 may adjust a focal point and a magnification by moving a lens in response to an operation amount of the operation switch 115.

The camera head 114 includes a color separation prism in an inside thereof. The color separation prism separates the light, which is converged by the relay lens 113, into four colors which are red light (R light), green light (G light), blue light (B light), and near-infrared light (IR light). The color separation prism is composed, for Example, of a translucent member such as glass.

The camera head 114 further includes the image sensor as a detector in the inside. For Example, four image sensors are provided, and the four image sensors convert optical images, which are individually formed on the imaging surfaces thereof, into electrical signals. The image sensors are not particularly limited; however, at least either one of charge coupled devices (CCDs) and complementary metal oxide semiconductors (CMOSs) can be used. Then, the four image sensors are dedicated sensors which receive pieces of light of a near-infrared component (IR component), a blue component (B component), a red component (R component), and a green component (G component).

In place of the color separation prism, the camera head 114 may include a color filter in the inside. The color filter is provided on the imaging surfaces of the image sensors. For Example, four color filters are provided, and the four color filters receive the light converged by the relay lens 113, and selectively allow penetration of the red light (R light), the green light (G light), the blue light (B light), and the near-infrared light (IR light).

It is preferable that the color filter that selectively allows penetration of the IR light be provided with a barrier film that cuts a reflection component of the near-infrared light (IR light), which is included in the illumination light. Thus, only the fluorescence emitted from the ICG and composed of the IR light will form an image on the imaging surface of the image sensor for the IR light. Therefore, it becomes easy to clearly observe an affected area that emits light by the ICG.

Figure 7:
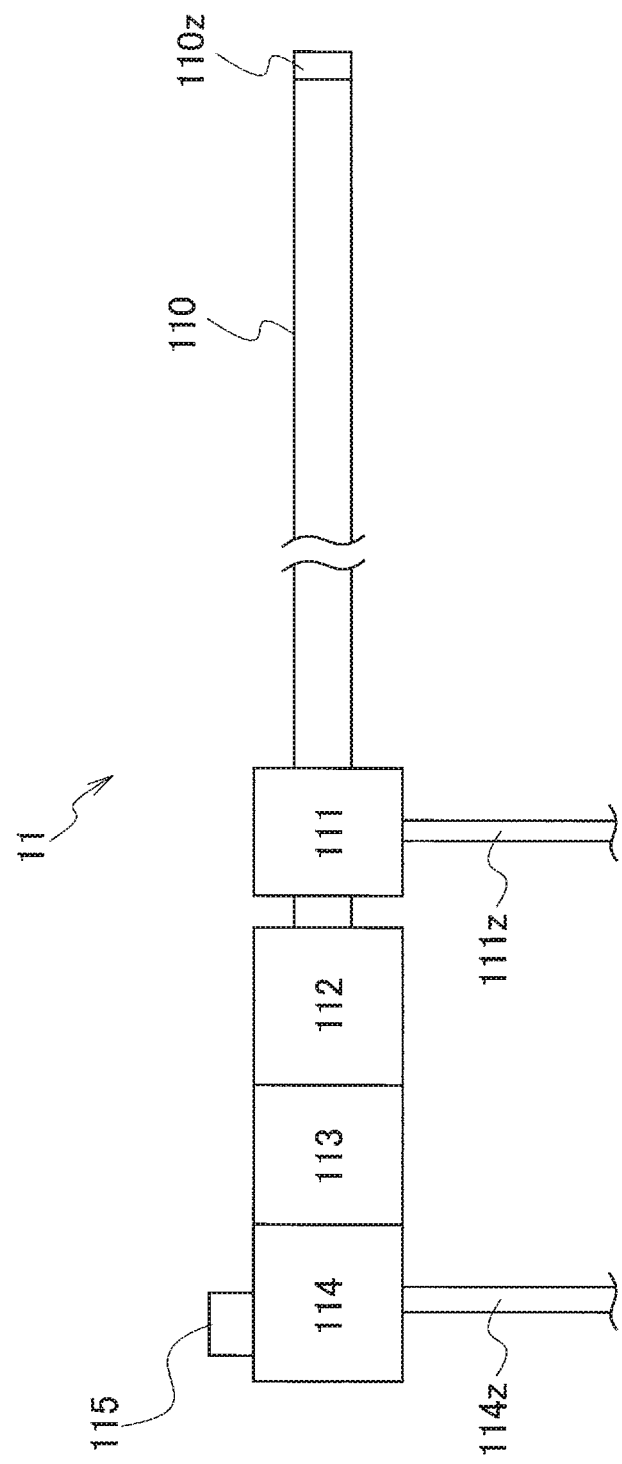
FIG. 7 is a diagram schematically illustrating a configuration of an endoscope according to this embodiment.

Note that, as illustrated in FIG. 7, to the camera head 114, connected is a signal cable 114z for transmitting the electrical signals, which are output from the image sensors, to a camera control unit (CCU) 12 to be described later.

In the endoscope 11 having such a configuration, light from the subject is guided to the relay lens 113 through the scope 110, and further, penetrates the color separation prism in the camera head 114, and forms images on the four image sensors.

(Endoscope System)

Figure 8:
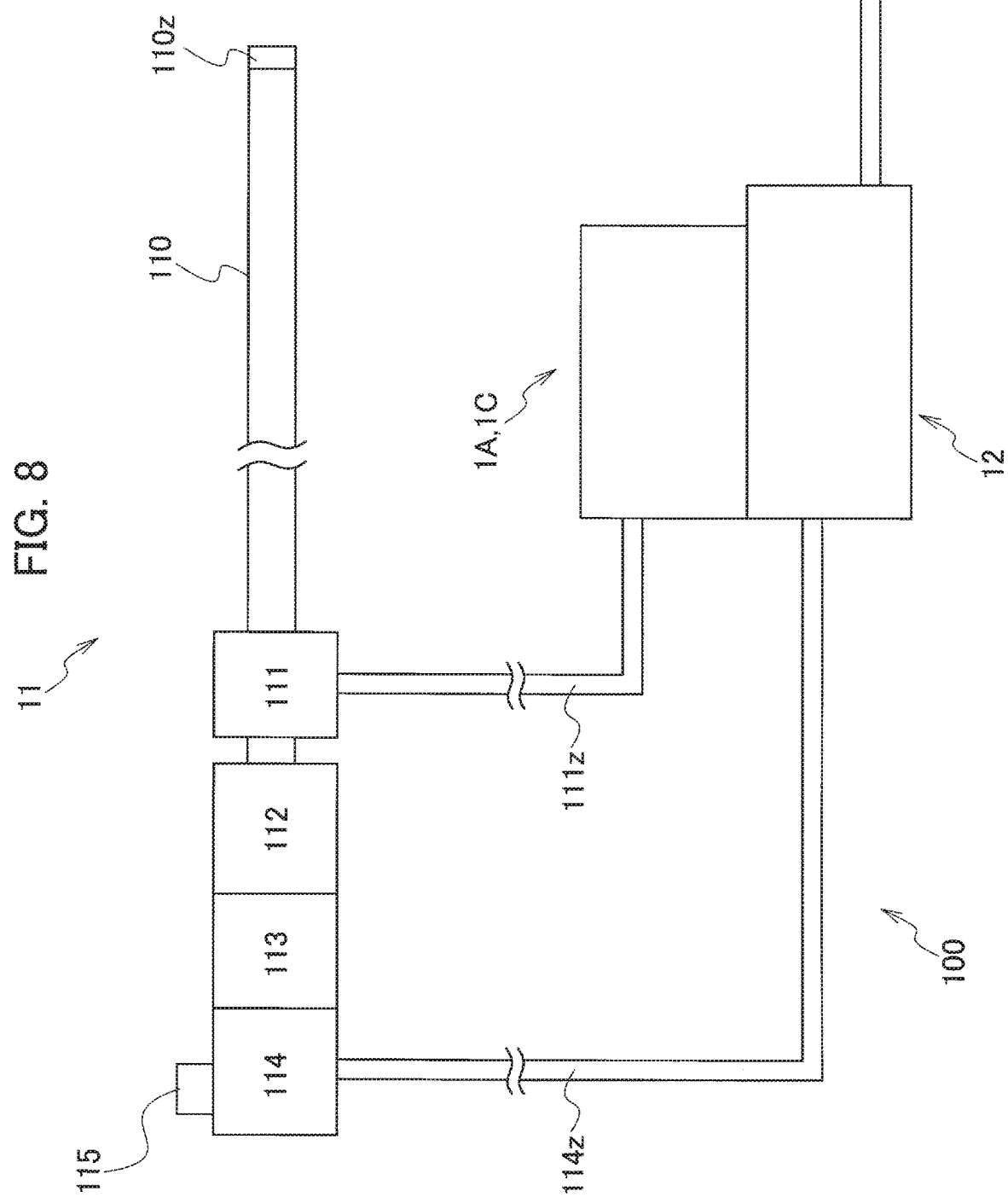
FIG. 8 is a diagram schematically illustrating a configuration of an endoscope system according to this embodiment.

As illustrated in FIG. 8, an endoscope system 100 includes the endoscope 11 that captures the inside of the subject, the camera control unit (CCU) 12, the light emitting device 1A or 1C, and a display device 13 such as a display.

The CCU 12 includes at least an RGB signal processing unit, an IR signal processing unit, and an output unit. Then, the CCU 12 executes a program held by a memory in the inside or outside of the CCU 12, thereby achieving the respective functions of the RGB signal processing unit, the IR signal processing unit, and the output unit.

The RGB signal processing unit converts electrical signals of the B component, the R component, and the G component, which are output from the image sensor, into video signals displayable on the display device 13, and output the video signals to the output unit. Moreover, the IR signal processing unit converts an electrical signal of the IR component, which is output from the image sensor, into a video signal, and outputs the video signal to the output unit.

The output unit outputs at least either one of the video signals of the respective RGB color components and the video signal of the IR component to the display device 13. For Example, the output unit outputs the video signals on the basis of either of a simultaneous output mode and a superposition output mode.

In the simultaneous output mode, the output unit simultaneously outputs an RGB image and an IR image on different screens. By the simultaneous output mode, the RGB image and the IR image can be compared with each other on the different screens, and an affected area can be observed. In the superposition output mode, the output unit outputs a synthetic image in which the RGB image and the IR image are superposed on each other. By the superposition output mode, for Example, an affected area, which has emitted light by the ICG, can be clearly observed in the RGB image.

On the basis of the video signals output from the CCU 12, the display device 13 displays an image of an object such as an affected area on a screen. In the case of the simultaneous output mode, the display device 13 divides the screen into a plurality of screens, and displays the RGB image and the IR image on the respective screens side by side. In the case of the superposition output mode, the display device 13 displays, by one screen, the synthetic image in which the RGB image and the IR image are superposed on each other.

Next, a description will be given of functions of the endoscope 11 and the endoscope system 100 according to this embodiment. In the case of observing a subject by using the endoscope system 100, first, the indocyanine green (ICG) that is a fluorescent drug is administered to the subject. Thus, the ICG is accumulated on a region (affected area) of a lymph node and a tumor.

Next, through the transmission cable 111z, visible light and near-infrared light are introduced into the light source connector 111 from the light emitting device 1A or 1C. Light introduced into the light source connector 111 is introduced into a distal end side of the scope 110, is projected from the imaging window 110z, and is thereby applied to the affected area and a periphery of the affected area. Light reflected by the affected area or the like and fluorescence emitted from the ICG are introduced to a rear end side of the scope 110 through the imaging window 110z and the optical fiber, is converged by the relay lens 113, and enters the color separation prism in the inside of the camera head 114.

In the light incident into the color separation prism, light of the IR component, which is separated by an IR separation prism, is formed as an optical image of an infrared light component by the image sensor for the IR. Light of the B component, which is separated by a blue separation prism, is formed as an optical image of a blue component by the image sensor for blue. Light of the R component, which is separated by a red separation prism, is formed as an optical image of a red component by the image sensor for red. Light of the G component, which is separated by a green separation prism, is formed as an optical image of a green component by the image sensor for green.

The electrical signal of the IR component, which is converted by the image sensor for IR, is converted into a video signal by the IR signal processing unit in the inside of the CCU 12. The respective electrical signals of the B component, the R component, and the G component, which are individually converted by the image sensors for RGB, are converted into the respective video signals by the RGB signal processing unit in the inside of the CCU 12. The video signal of the IR component and the respective video signals of the B component, the R component, and the G component are output to the display device 13 in synchronization with one another.

When the simultaneous output mode is set in the inside of the CCU 12, the RGB image and the IR image are simultaneously displayed by two screens on the display device 13. Moreover, when the superposition output mode is set in the inside of the CCU 12, the synthetic image in which the RGB image and the IR image are superposed on each other is displayed on the display device 13.

As described above, the endoscope 11 of this embodiment includes the endoscope light emitting device 1, 1A, 1B or 1C. Therefore, the fluorescent drug is efficiently excited and emitted by using the endoscope 11, thus making is possible to clearly observe the affected area.

It is preferable that the endoscope 11 of this embodiment further include a detector that detects the fluorescence emitted from the fluorescent drug that has absorbed the first wavelength-converted light 7. In addition to the light emitting device 1, 1A, 1B or 1C, the endoscope 11 integrally includes the detector that detects the fluorescence emitted from the fluorescent drug, whereby the affected area can be specified by only the endoscope. Therefore, it is not necessary to largely open the stomach and specify the affected area as heretofore, and accordingly, it becomes possible to perform examination and treatment, which give less burden to a patient. Moreover, a doctor who uses the endoscope 11 can grasp the affected area accurately, and accordingly, it becomes possible to improve treatment efficiency.

[Fluorescence Imaging Method]

Next, a description will be given of a fluorescence imaging method according to this embodiment. The fluorescence imaging method of this embodiment is a method using the endoscope light emitting device 1, 1A, 1B or 1C or the endoscope 11, which is mentioned above, and includes the steps of administering a fluorescent drug to a subject; and applying the first wavelength-converted light 7 to the subject has made contact with the fluorescent drug.

In the fluorescence imaging method of this embodiment, first, the fluorescent drug is administered to the subject, and the fluorescent drug is specifically accumulated on an affected area in the subject. As the fluorescent drug to be administered to the subject, as mentioned above, a drug can be used, which absorbs excitation light in the near-infrared light region, and further emits fluorescence in the near-infrared light region, the fluorescence having a longer wavelength than the excitation light. As the fluorescent drug, for Example, at least one selected from the group consisting of indocyanine green (ICG), a phthalocyanine-based compound, a talaporfin sodium-based compound, and a dipicolylcyanine (DIPCY)-based compound can be used.

Next, the first wavelength-converted light 7 is applied to the subject with whom the fluorescent drug has made contact. As mentioned above, the first wavelength-converted light 7 is emitted from the endoscope light emitting device 1, 1A, 1B or 1C or the endoscope 11, and has a light component across at least the wavelength range of 700 nm or more and 800 nm or less. Then, as mentioned above, the light in the near-infrared light region is difficult to be scattered by hemoglobin and water in a living body, and is easy to penetrate the living body, and accordingly, the first wavelength-converted light 7 penetrates the living body and excites the fluorescent drug. The excited fluorescent drug emits fluorescence in the near-infrared light region, the fluorescence having a longer wavelength than the excitation light. Then, the fluorescence emitted from the fluorescent drug is detected by using the detector, thus making it possible to observe and treat the affected area in the living body.

As mentioned above, the first wavelength-converted light 7 has a light component across at least the whole of the wavelength range of 700 nm or more and 800 nm or less, and accordingly, becomes capable of exciting the fluorescent drug with high efficiency even when the fluorescent drug varies in characteristics. Moreover, when the solid-state light emitting element 2 of each of the endoscope light emitting devices 1, 1A, 1B and 1C radiates laser light, an intensity of the first wavelength-converted light 7 emitted from the first phosphor 4 becomes high. Therefore, it becomes possible to excite the fluorescent drug in the subject with higher efficiency, and to radiate the long-wavelength fluorescence.

EXAMPLES

Hereinafter, the light emitting device of this embodiment will be described more in detail by Examples; however, this embodiment is not limited to these.

[Preparation of Phosphor]

Example 1

An oxide phosphor for use in Example 1 was synthesized by using a preparation method using a solid phase reaction. The phosphor of Example 1 is an oxide phosphor represented by a composition formula of $(Y_{0.98}Ce_{0.02})_3Mg_2(AlO_4)(SiO_4)_2$. Note that the following compound powders were used as main raw materials at the time of synthesizing the oxide phosphor.

Yttrium oxide ($Y_2O_3$): purity 3N, Shin-Etsu Chemical Co., Ltd.

Cerium oxide ($CeO_2$): purity 4N, Shin-Etsu Chemical Co., Ltd.

Aluminum oxide ($\theta$-$Al_2O_3$): purity>4N5, Sumitomo Chemical Co., Ltd.

Magnesium oxide (MgO): purity 4N, Kojundo Chemical Laboratory Co., Ltd.

Silicon dioxide ($SiO_2$): purity>3N, Nippon Aerosil Co., Ltd.

Note that, for the purpose of improving reactivity between the raw materials, AKP-G008 made by Sumitomo Chemicals Co., Ltd. was used as aluminum oxide. Moreover, in the Example, the following compound powders were used as reaction accelerators.

Aluminum fluoride ($AlF_3$): purity 3N, Kojundo Chemical Laboratory Co., Ltd.

Calcium carbonate ($K_2CO_3$): purity 2N5, Kanto Chemical Co., Inc.

First, the above-described raw materials were weighed so as to obtain a compound with a stoichiometric composition, which is $(Y_{0.98}Ce_{0.02})_3Mg_2(AlO_4)(SiO_4)_2$. Next, by using a ball mill, the weighed raw materials and a trace amount of the reaction accelerators were wet-mixed together with an appropriate amount of water (pure water) sufficiently. The mixed raw materials thus obtained were transferred to a container, and were dried all night at 120° C. by using a dryer. Then, the mixed raw materials already dried were pulverized by using a mortar and a pestle, and were prepared as a raw material to be fired.

The above-described raw material to be fired was transferred to a small alumina crucible attached with a cover, and was fired for 4 hours in an atmosphere of 1600° C. by using a box-type electric furnace, and thereafter, a fired product was lightly disintegrated. The disintegrated fired product was transferred to the small alumina crucible one more time. Next, the small alumina crucible that contained the fired product was put into the inside of a little larger alumina crucible that contains carbon, and the crucible was closed. Then, the alumina crucible was fired at 1400° C. for two hours by using a box-type electric furnace. As described above, the fired product was subjected to reduction treatment by CO gas generated by the firing at 1400° C., whereby a phosphor of this Example was obtained. A color of the obtained phosphor was dark orange. Note that post-treatment was omitted due to experimental reasons.

Example 2, Example 3

Nitride phosphors for use in Example 2 and Example 3 were synthesized by using a preparation method using a solid phase reaction. The phosphor of Example 2 is a nitride phosphor represented by a composition formula of $La_{2.991}Ce_{0.009}(Si,A)_6(N,O)_{11-x}$. Moreover, the phosphor of Example 3 is a nitride phosphor represented by a composition formula of $La_{2.982}Ce_{0.012}(Si,A)_6(N,O)_{11-x}$.

At the time of synthesizing the nitride phosphor, lanthanum nitride (III) (LaN), silicon nitride powder ($Si_3N_4$), aluminum nitride powder (AlN), and cerium fluoride powder ($CeF_3$) were used as main raw materials.

First, the above-described raw materials were weighed so as to form a compound with a stoichiometric composition, which is $La_{2.991}Ce_{0.009}(Si,Al)_6(N,O)_{11-x}$, $La_{2.982}Ce_{0.012}(Si,Al)_6(N,O)_{11-x}$. However, the LaN powder was weighed to an amount larger by 24% than a stoichiometric value thereof.

Next, the weighed raw materials were dry-mixed with one another by using a mortar in a glove box under a nitrogen atmosphere. A mixed raw material thus obtained was put into a crucible made of boron nitride, and was fired at 1900° C. for 2 hours under a nitrogen atmosphere of 0.5 MPa. Then, a fired product after the firing was washed for 1 hour in a nitric acid solution with a concentration of 10%. Thus, the phosphors of Example 2 and Example 3 were obtained.

Example 4

An oxide phosphor for use in Example 4 was synthesized by using a preparation method using a solid phase reaction. The phosphor of Example 4 is an oxide phosphor represented by a composition formula of $(Ca_{0.1}Sr_{0.897}Eu_{0.003})Sc_2O_4$. Note that, the following compound powders were used as main raw materials at the time of synthesizing the oxide phosphor.

Calcium carbonate ($CaCO_3$): purity 3N, Wako Pure Chemical Industries, Ltd.

Strontium carbonate ($SrCO_3$): purity 3N, Wako Pure Chemical Industries, Ltd.

Scandium oxide ($Sc_2O_3$): purity 3N, Shin-Etsu Chemical Co., Ltd.

Europium oxide ($Eu_2O_3$): purity 3N, Shin-Etsu Chemical Co, Ltd.

First, the above-described raw materials were weighed so as to obtain a compound with a stoichiometric composition, which is $(Ca_{0.1}Sr_{0.897}Eu_{0.003})Sc_2O_4$. Next, the weighed raw materials were put into a beaker into which pure water was poured, and were stirred for 1 hour by using a magnetic stirrer. Thus, a slurry-like mixed raw material made of pure water and the raw materials was obtained. Thereafter, the slurry-like mixed raw material was fully dried by using a dryer. Then, the mixed raw materials already dried were pulverized by using a mortar and a pestle, and were prepared as a raw material to be fired.

The above-described raw material to be fired was transferred to a small alumina crucible, and was subjected to reduction treatment for 1 hour in an atmosphere of 1500° C. reducing gas (96 vol % $N_2$+4 vol % $H_2$) by using a tubular atmosphere furnace, whereby a phosphor of this Example was obtained. Note that a flow rate of the reducing gas was set to 1 L/min, and a heating/cooling rate was set to 300° C./h.

Note that a color of the obtained phosphor was light purple. This suggests that the phosphor of Example 4 absorbs visible light other than violet light (for Example, the visible light is blue light, green light, yellow light, and red light) relatively intensely.

Example 5

A nitride phosphor for use in Example 5 was synthesized by using a preparation method using a solid phase reaction. The phosphor of Example 5 is a nitride phosphor represented by a composition formula of $(La_{0.896}Gd_{0.1}Ce_{0.004})_3(Si,Al)_6(N,O)_{11-x}$.

At the time of synthesizing the nitride phosphor, lanthanum nitride (III) (LaN), gadolinium nitride (III) (GdN), silicon nitride powder ($Si_3N_4$), aluminum nitride powder (AlN), and cerium nitride powder (CeN) were used as main raw materials.

First, the above-described raw materials were weighed so as to form a compound with a stoichiometric composition, which is $(La_{0.896}Gd_{0.1}Ce_{0.004})_3(Si,Al)_6(N,O)_{11-x}$. Next, the weighed raw materials were dry-mixed with one another by using a mortar in a glove box under a nitrogen atmosphere. A mixed raw material thus obtained was put into a crucible made of boron nitride, and was fired at 1900° C. for 2 hours under a nitrogen atmosphere of 0.5 MPa. Then, a fired product after the firing was washed for 1 hour in a nitric acid solution with a concentration of 10%. Thus, the phosphor of Example 5 was obtained. Note that a color of the obtained phosphor was light red.

Example 6

An oxide phosphor for use in Example 6 was synthesized by using a preparation method using a solid phase reaction. The phosphor of Example 6 is an oxide phosphor represented by a composition formula of $Gd_3(Ga_{0.97}Cr_{0.03})_2Ga_3O_{12}$. Moreover, the phosphor of Example 6 is a $Cr^{3+}$-activated phosphor. Then, the following compound powders were used as main raw materials at the time of synthesizing the oxide phosphor of Example 6.

Gadolinium oxide ($Gd_2O_3$): purity 3N, Wako Pure Chemical Industries, Ltd.

Gallium oxide ($Ga_2O_3$): purity 4N, Wako Pure Chemical Industries, Ltd.

Chromium oxide ($Cr_2O_3$): purity 3N, Kojundo Chemical Laboratory Co., Ltd.

First, the above-described raw materials were weighed so as to obtain a compound with a stoichiometric composition, which is $Gd_3(Ga_{0.97}Cr_{0.03})_2Ga_3O_2$. Next, the weighed raw materials were put into a beaker into which pure water was poured, and were stirred for 1 hour by using a magnetic stirrer. Thus, a slurry-like mixed raw material made of pure water and the raw materials was obtained. Thereafter, the slurry-like mixed raw material was fully dried by using a dryer. Then, the mixed raw materials already dried were pulverized by using a mortar and a pestle, and were prepared as a raw material to be fired.

The above-described raw material to be fired was transferred to a small alumina crucible, and was fired for 1 hour in the atmosphere of 1500° C. by using a box-type electric furnace, whereby a phosphor of this Example was obtained. Note that a heating/cooling rate was set to 400° C./h. A color of the obtained phosphor was dark green.

Example 7

An oxide phosphor for use in Example 7 was synthesized by using a preparation method using a solid phase reaction. The phosphor of Example 7 is an oxide phosphor represented by a composition formula of $(Gd_{0.75}La_{0.25})_3(Ga_{0.97}Cr_{0.03})_2Ga_3O_{12}$. Moreover, the phosphor of Example 7 is a $Cr^{3+}$-activated phosphor. Then, the following compound powders were used as main raw materials at the time of synthesizing the oxide phosphor of Example 7.

Gadolinium oxide ($Gd_2O_3$): purity 3N, Wako Pure Chemical Industries, Ltd.

Lanthanum oxide ($La_2O_3$): purity 3N, Wako Pure Chemical Industries, Ltd.

Gallium oxide ($Ga_2O_3$): purity 4N, Wako Pure Chemical Industries, Ltd.

Chromium oxide ($Cr_2O_3$): purity 3N, Kojundo Chemical Laboratory Co., Ltd.

First, the above-described raw materials were weighed so as to obtain a compound with a stoichiometric composition, which is $(Gd_{0.75}La_{0.25})_3(Ga_{0.97}Cr_{0.03})_2Ga_3O_{12}$. Next, the weighed raw materials were put into a beaker into which pure water was poured, and were stirred for 1 hour by using a magnetic stirrer. Thus, a slurry-like mixed raw material made of pure water and the raw materials was obtained. Thereafter, the slurry-like mixed raw material was fully dried by using a dryer. Then, the mixed raw materials already dried were pulverized by using a mortar and a pestle, and were prepared as a raw material to be fired.

The above-described raw material to be fired was transferred to a small alumina crucible, and was fired for 1 hour in the atmosphere of 1450° C. by using a box-type electric furnace, whereby a phosphor of this Example was obtained. Note that a heating/cooling rate was set to 400° C./h. A color of the obtained phosphor was dark green.

[Evaluation]

(Crystal Structure Analysis)

A crystal structure of the phosphor of Example 1 was evaluated by using an X-ray diffractometer (X'Pert PRO; made by PANalytical Ltd. in Spectris Co., Ltd.)

Although details are omitted, as a result of the evaluation, it has been found out that the phosphor of Example 1 is composed by containing, as a main component, a compound having a crystal structure of garnet. That is, it has been found out that the phosphor of Example 1 is a garnet phosphor. In such a way, it was confirmed that the phosphor of Example 1 is $(Y_{0.98}Ce_{0.02})_3Mg_2(AlO_4)(SiO_4)_2$ as a compound.

Next, crystal structures of the phosphors of Example 2 and Example 3 were evaluated by using an X-ray diffractometer (RINT2100; made by Rigaku Corporation).

Although details are omitted, as a result of the evaluation, it has been found out that the phosphors of Example 2 and Example 3 re composed by containing, as a main component, a compound having a tetragonal crystal system. Then, it has been found out that each of the phosphors has almost the same crystal structure as a crystal of nitride represented by a general formula $La_3Si_6N_{11}$. That is, it has been found out that the phosphors of Example 2 and Example 3 are nitride phosphors. In such a way, it was confirmed that the phosphors of Example 2 and Example 3 are $La_{2.991}Ce_{0.009}(Si,Al)_6(N,O)_{11-x}$, and $La_{2.982}Ce_{0.012}(Si,Al)_6(N,O)_{11-x}$ as compounds, respectively.

Next, a crystal structure of the phosphor of Example 4 was evaluated by using an X-ray diffractometer (MiniFlex; made by Rigaku Corporation).

Figure 9:
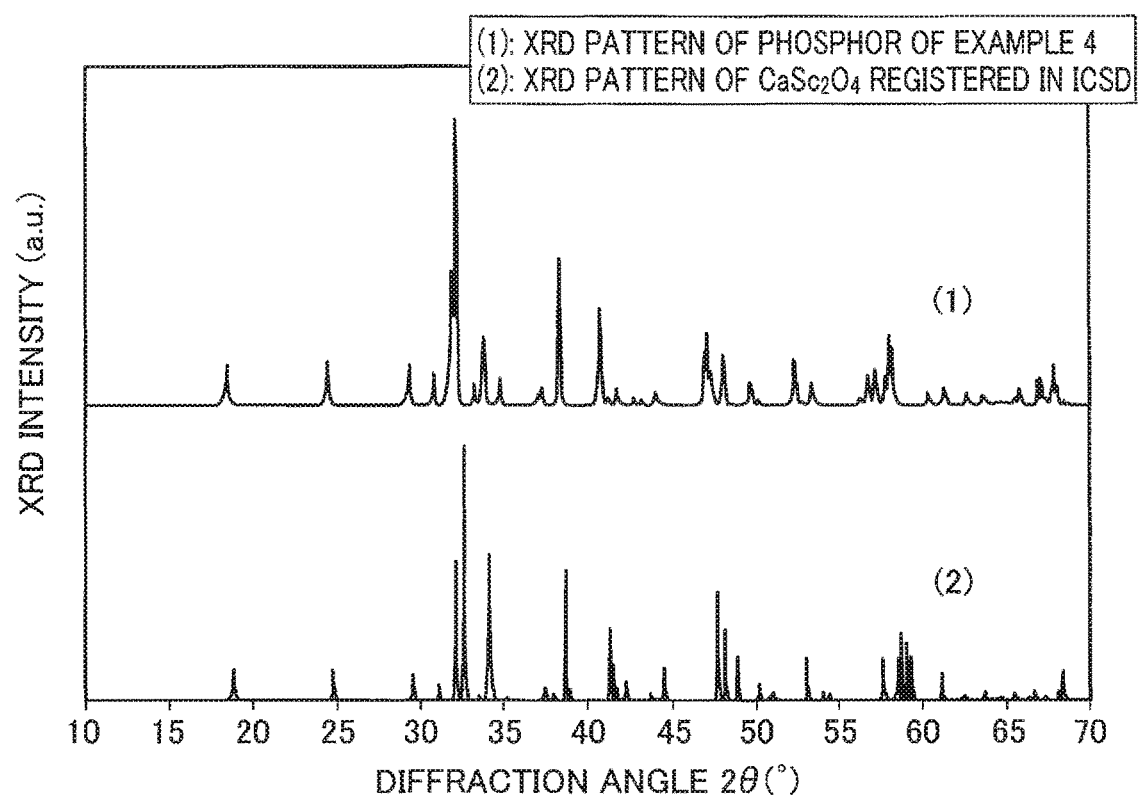
FIG. 9 is a graph illustrating an X-ray diffraction pattern of a phosphor used in a light emitting device of Example 4 and a pattern of $CaSc_2O_4$ registered in the Inorganic Crystal structure Database (ICSD).

FIG. 9 illustrates an X-ray diffraction (XRD) pattern of the phosphor of Example 4 ((1) in FIG. 9). For reference, FIG. 9 also illustrates a pattern of $CaSc_2O_4$, which is registered in the Inorganic Crystal structure Database (ICSD) ((2) in FIG. 9). As seen from FIG. 9, an XRD pattern of the phosphor of Example 4 coincided with the pattern of $CaSc_2O_4$, which is registered in the ICSD. This represents that the phosphor of Example 4 is a compound having a calcium ferrite-type crystal structure that is the same as that of $CaSc_2O_4$.

Note that a diffraction peak of the phosphor of Example 4 was located on a low angle side in comparison with a diffraction peak of $CaSc_2O_4$, which is registered in the ICSD. A low angle shift of the diffraction peak indicates an increase of a lattice interplanar spacing value (d value) of the crystal. Therefore, this result suggests that $Sr^{2+}$ (ionic radius: 1.26 Å; coordination: 8) with a relatively large ionic radius was substituted for a part of $Ca^{2+}$ (ionic radius: 1.12 Å; coordination: 8) of a $CaSc_2O_4:Eu^{2+}$ phosphor, and that a lattice interval of the crystal was increased. From the above result, Example 4 is regarded as an oxide phosphor represented by a composition formula of $(Ca_{0.1}Sr_{0.897}Eu_{0.003})Sc_2O_4$.

Next, a crystal structure of the phosphor of Example 5 was evaluated by using an X-ray diffractometer (MiniFlex; made by Rigaku Corporation).

Although details are omitted, as a result of the evaluation, it has been found out that the phosphor of Example 5 is composed by containing, as a main component, a compound having a tetragonal crystal system. Then, it has been found out that the phosphor of Example 5 has almost the same crystal structure as a crystal of nitride represented by a general formula $La_3Si_6N_{11}$. That is, it has been found out that the phosphor of Example 5 is a nitride phosphor. In such a way, it was confirmed that the phosphor of Example 5 is $(La_{0.896}Gd_{0.1}Ce_{0.004})_3(Si,Al)_6(N,O)_{11-x}$ as a compound.

Next, a crystal structure of the phosphor of Example 6 was evaluated by using an X-ray diffractometer (MiniFlex; made by Rigaku Corporation).

Although details are omitted, as a result of the evaluation, it has been found out that the phosphor of Example 6 is composed by containing, as a main component, a compound having a crystal structure of garnet. That is, it has been found out that the phosphor of Example 6 is a garnet phosphor. In such a way, it was confirmed that the phosphor of Example 6 is $Gd_3(Ga_{0.97}Cr_{0.03})_2Ga_3O_{12}$ as a compound.

Next, a crystal structure of the phosphor of Example 7 was evaluated by using an X-ray diffractometer (MiniFlex; made by Rigaku Corporation).

Although details are omitted, as a result of the evaluation, it has been found out that the phosphor of Example 7 is composed by containing, as a main component, a compound having a crystal structure of garnet. That is, it has been found out that the phosphor of Example 7 is a garnet phosphor. In such a way, it was confirmed that the phosphor of Example 7 is $(Gd_{0.75}La_{0.25})_3(Ga_{0.97}Cr_{0.03})_2Ga_3O_{12}$ as a compound.

(Spectral Characteristics)

Figure 10:
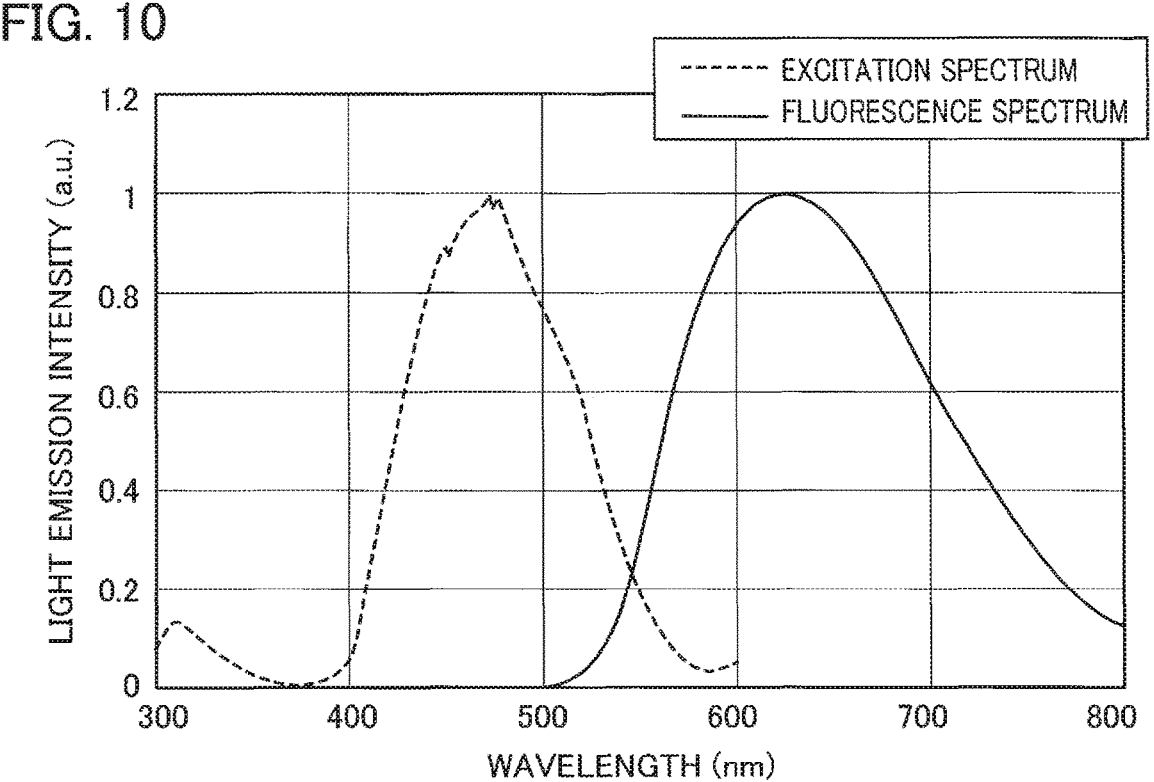
FIG. 10 is a graph illustrating an excitation spectrum and light emission spectrum of a phosphor used in a light emitting device of Example 1.

Next, excitation characteristics and fluorescence characteristics of the phosphor of Example 1 were evaluated by using a spectrophotofluorometer (FP-6500; made by JASCO Corporation). FIG. 10 illustrates an excitation spectrum and fluorescence spectrum of the phosphor of Example 1. Note that an excitation wavelength at the time of measuring the fluorescence spectrum was set to 450 nm, and a monitor wavelength at the time of measuring the excitation spectrum was set to a fluorescence peak wavelength. Moreover, in FIG. 10, both of the fluorescence spectrum and the excitation spectrum are standardized and shown while taking peak values thereof as 1.

The fluorescence spectrum of the phosphor of Example 1 was a broad spectrum that can be regarded to result from the $5d^1 \rightarrow 4f^1$ transition of $Ce^{3+}$. Then, the fluorescence spectrum of the phosphor of Example 1 formed a band spectrum across the whole of a wavelength range of 600 nm or more and 800 nm or less.

Note that peak wavelengths of the fluorescence spectrum and excitation spectrum of the phosphor of Example 1 were 625 nm and 473 nm, respectively. This represents that the phosphor of Example 1 can efficiently absorb blue light with a wavelength of around 430 to 480 nm and can perform wavelength conversion for the absorbed blue light into fluorescence that forms a band spectrum across the whole of the wavelength range of 600 nm or more and 800 nm or less.

Figure 11:
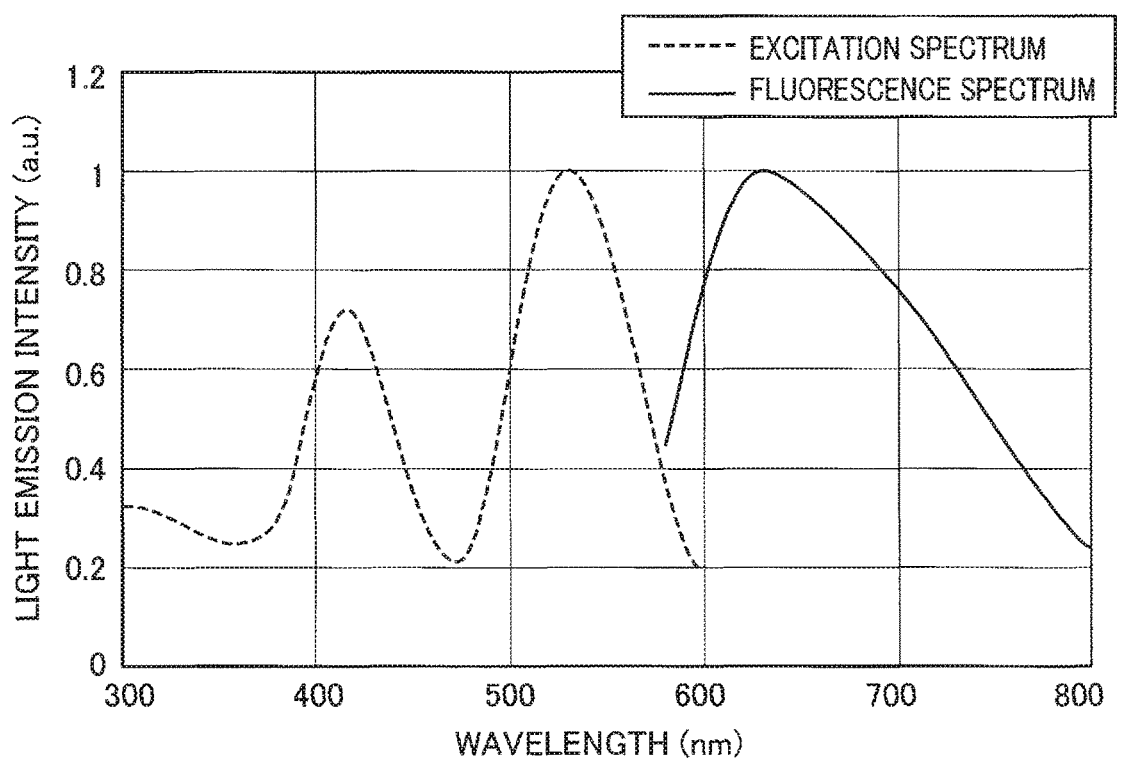
FIG. 11 is a graph illustrating an excitation spectrum and light emission spectrum of a phosphor used in a light emitting device of Example 2.

Next, similarly to Example 1, excitation characteristics and fluorescence characteristics of the phosphor of Example 2 were evaluated by using a spectrophotofluorometer. FIG. 11 illustrates an excitation spectrum and fluorescence spectrum of the phosphor of Example 2. Note that an excitation wavelength at the time of measuring the fluorescence spectrum was set to 540 nm, and a monitor wavelength at the time of measuring the excitation spectrum was set to a fluorescence peak wavelength. Moreover, in FIG. 11, both of the fluorescence spectrum and the excitation spectrum are standardized and shown while taking peak values thereof as 1.

The fluorescence spectrum of the phosphor of Example 2 was a broad spectrum that can be regarded to result from the $5d^1 \rightarrow 4f^1$ transition of $Ce^{3+}$. Then, the fluorescence spectrum of the phosphor of Example 2 formed a band spectrum across the whole of the wavelength range of 600 nm or more and 800 nm or less.

Note that peak wavelengths of the fluorescence spectrum and excitation spectrum of the phosphor of Example 2 were 630 nm and 531 nm, respectively. This represents that the phosphor of Example 2 can efficiently absorb green to yellow light with a wavelength of around 510 nm to 560 nm and can perform wavelength conversion for the absorbed green to yellow light into fluorescence that forms a band spectrum across the whole of the wavelength range of 600 nm or more and 800 nm or less.

Figure 12:
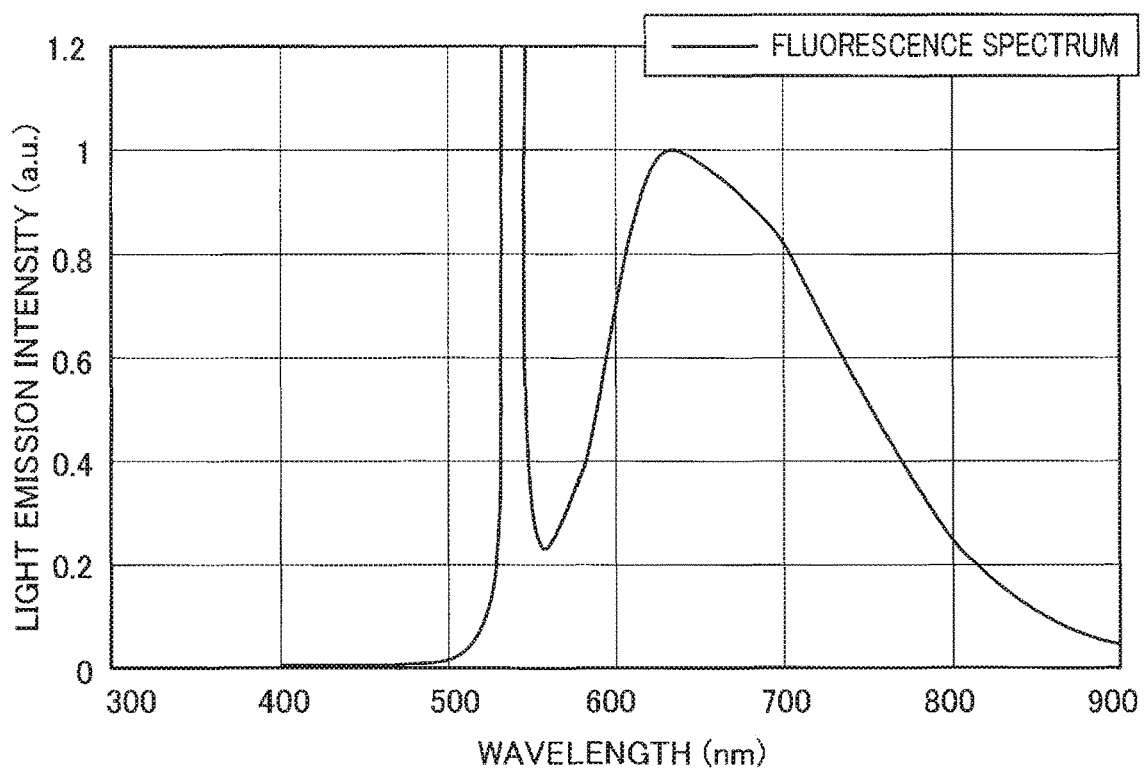
FIG. 12 is a graph illustrating a light emission spectrum of a phosphor used in a light emitting device of Example 3.

Next, similarly to Example 1, fluorescence characteristics of the phosphor of Example 3 were evaluated by using a spectrophotofluorometer. FIG. 12 illustrates a fluorescence spectrum of the phosphor of Example 3. Note that an excitation wavelength when the fluorescence spectrum was measured was set to 540 nm. Moreover, in FIG. 12, the fluorescence spectrum is standardized and shown while taking a peak value thereof as 1. Note that a sharp spectrum at around 540 nm in FIG. 12 is a light component of monochrome light used as excitation light, the light component having been reflected by the phosphor.

The fluorescence spectrum of the phosphor of Example 3 was a broad spectrum that can be regarded to result from the $5d^1 \rightarrow 4f^1$ transition of $Ce^{3+}$. Then, the fluorescence spectrum of the phosphor of Example 3 formed a band spectrum across the whole of the wavelength range of 600 nm or more and 800 nm or less. A peak wavelength in the fluorescence spectrum of the phosphor of Example 3 was 634 nm.

The above represents that the phosphor of Example 3 can absorb light with a single wavelength of around 540 nm and can perform wavelength conversion for the absorbed light into fluorescence that forms a band spectrum across the whole of the wavelength range of 600 nm or more and 800 nm or less.

Figure 13:
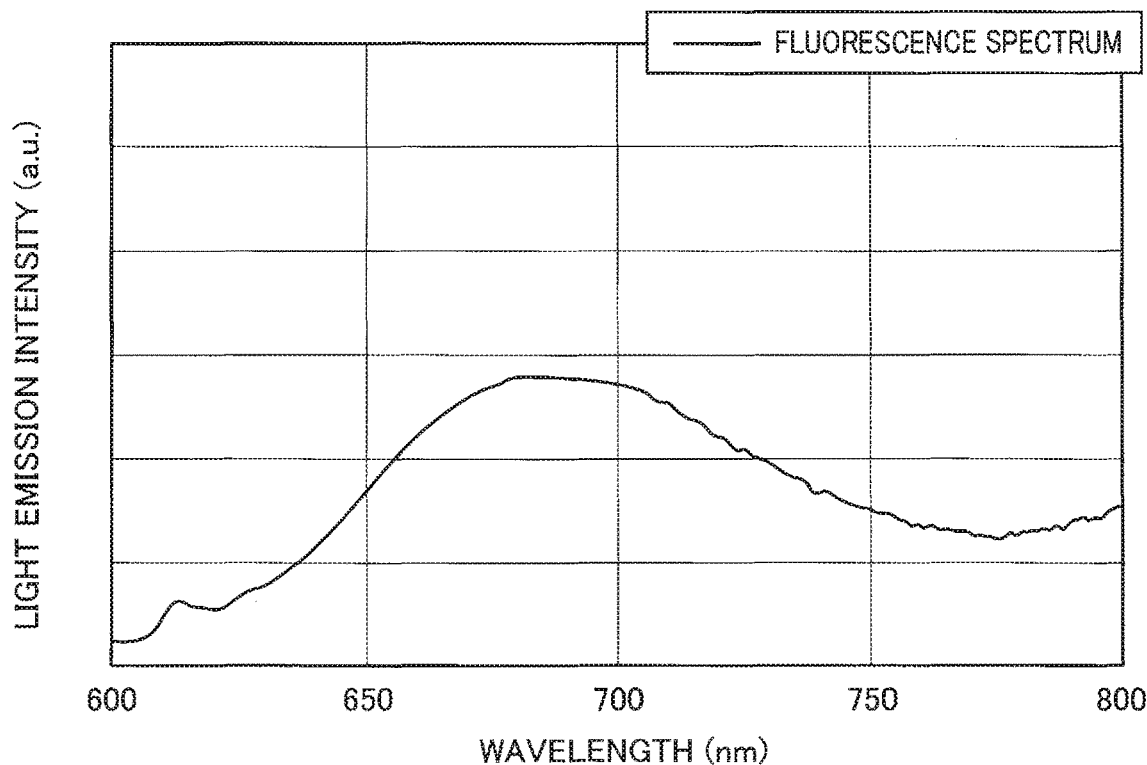
FIG. 13 is a graph illustrating a light emission spectrum of the phosphor used in the light emitting device of Example 4.

Next, fluorescence characteristics of the phosphor of Example 4 was evaluated by using a spectrophotofluorometer. FIG. 13 illustrates a fluorescence spectrum of the phosphor of Example 4. Note that an excitation wavelength when the fluorescence spectrum was measured was set to 460 nm.

The fluorescence spectrum of the phosphor of Example 4 was a broad spectrum that can be regarded to result from the $4f^65d^1 \rightarrow 4f^7$ transition of $Eu^{2+}$. Then, the fluorescence spectrum of the phosphor of Example 4 was a spectrum that can be regarded to form a band spectrum across the whole of a wavelength range of 700 nm or more and 800 nm or less. For those skilled in the art, it is obvious that, though a component of a long wavelength in the fluorescence spectrum of the phosphor of Example 4 contains some noise, a light component is present across the whole of the wavelength range of 700 nm or more and 800 nm or less.

The above represents that the phosphor of Example 4 can absorb blue light with a wavelength of around 460 nm and can perform wavelength conversion for the absorbed blue light into fluorescence that forms a band spectrum across the whole of the wavelength range of 700 nm or more and 800 nm or less. Note that a full width at half maximum in the fluorescence spectrum of the phosphor of Example 4 was approximately 100 nm.

Figure 14:
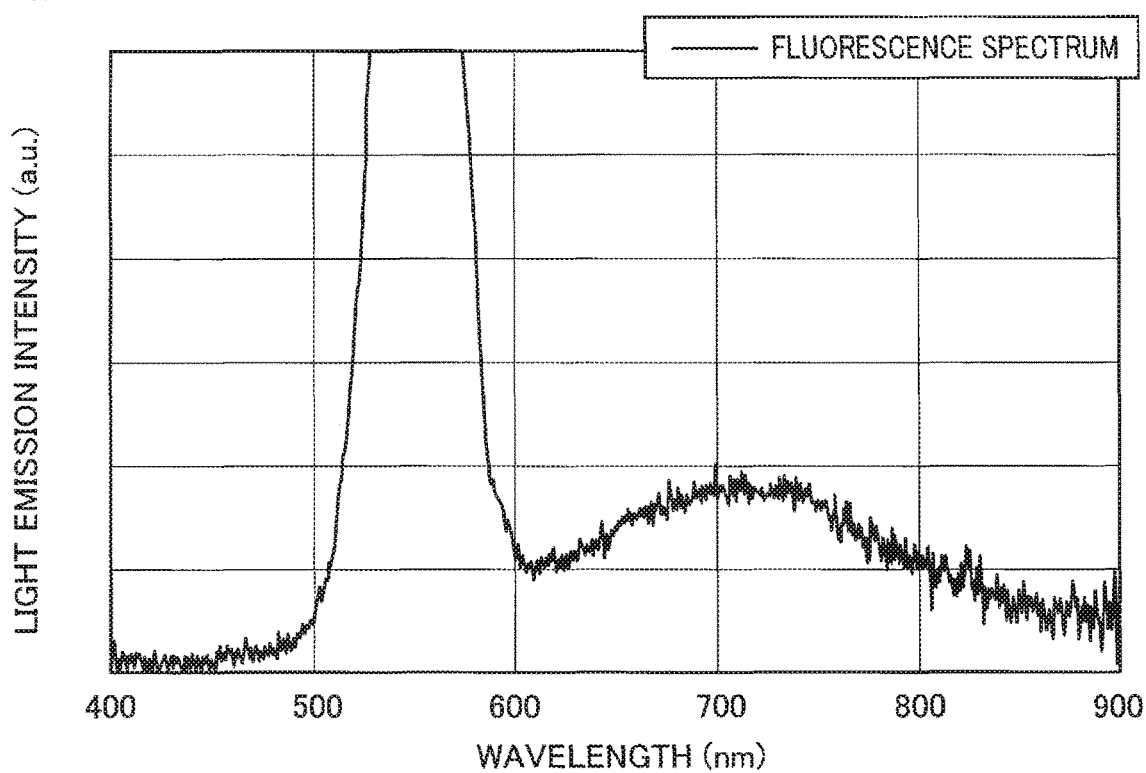
FIG. 14 is a graph illustrating a light emission spectrum of a phosphor used in a light emitting device of Example 5.

Next, fluorescence characteristics of the phosphor of Example 5 was evaluated by using a spectrophotofluorometer. FIG. 14 illustrates a fluorescence spectrum of the phosphor of Example 5. Note that an excitation wavelength when the fluorescence spectrum was measured was set to 540 nm. A sharp spectrum at around 540 nm in FIG. 14 is a light component of monochrome light used as excitation light, the light component having been reflected by the phosphor.

The fluorescence spectrum of the phosphor of Example 5 was a broad spectrum that can be regarded to result from the $5d^1 \rightarrow 4f^1$ transition of $Ce^{3+}$. Then, the fluorescence spectrum of the phosphor of Example 5 was a spectrum that can be regarded to form a band spectrum across at least the whole of the wavelength range of 700 nm or more and 800 nm or less. Moreover, the fluorescence spectrum of the phosphor of Example 5 was also a spectrum that can be regarded to form a band spectrum across the whole of the wavelength range of 600 nm or more and 800 nm or less.

The above represents that the phosphor of Example 5 can absorb green light with a wavelength of around 540 nm and can perform wavelength conversion for the absorbed green light into fluorescence that forms a band spectrum across the whole of the wavelength range of 700 nm or more and 800 nm or less. Moreover, the above represents that the phosphor of Example 5 can absorb green light with a wavelength of around 540 nm and can perform wavelength conversion for the absorbed green light into fluorescence that forms a band spectrum across the whole of the wavelength range of 600 nm or more and 800 nm or less. Note that a full width at half maximum in the fluorescence spectrum of the phosphor of Example 5 was approximately 160 nm.

Figure 15:
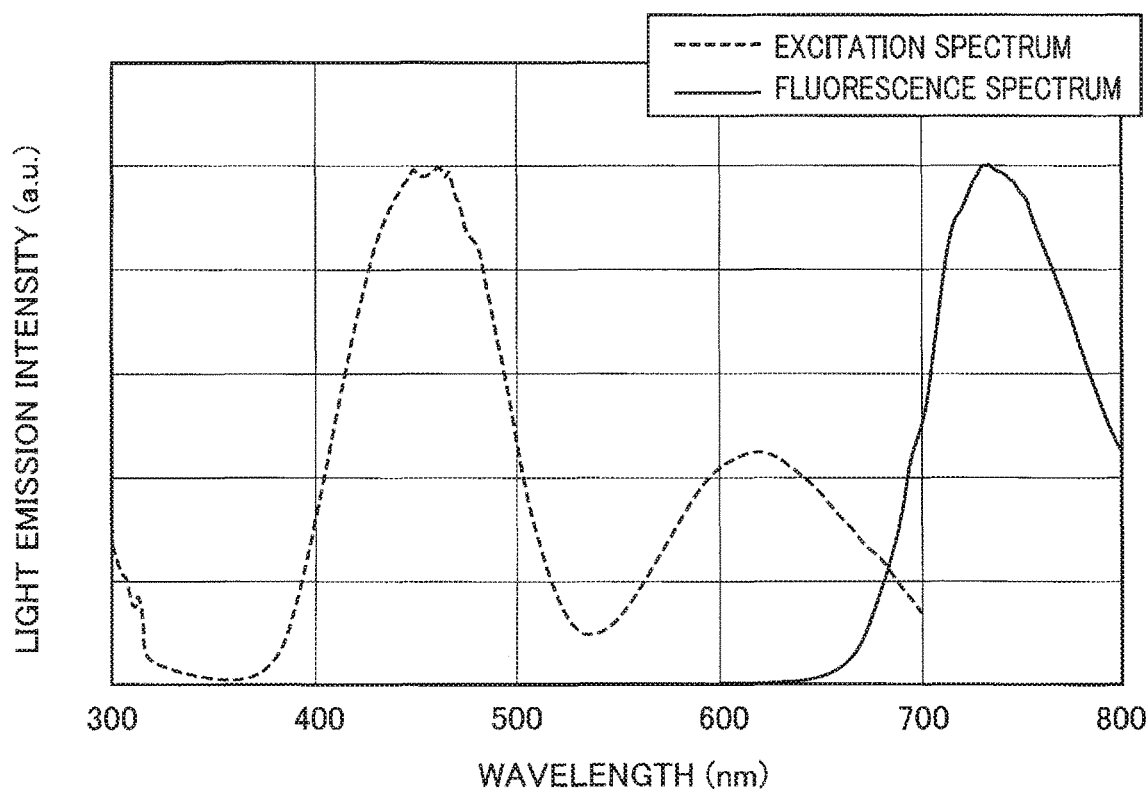
FIG. 15 is a graph illustrating an excitation spectrum and light emission spectrum of a phosphor used in a light emitting device of Example 6.

Next, excitation characteristics and fluorescence characteristics of the phosphor of Example 6 was evaluated by using a spectrophotofluorometer. FIG. 15 illustrates an excitation spectrum and fluorescence spectrum of the phosphor of Example 6. Note that an excitation wavelength at the time of measuring the fluorescence spectrum was set to 450 nm, and a monitor wavelength at the time of measuring the excitation spectrum was set to a fluorescence peak wavelength. In FIG. 15, light emission intensities of the fluorescence spectrum and the excitation spectrum are standardized and shown so as to be equal to each other.

The fluorescence spectrum of the phosphor of Example 6 was a broad spectrum that can be regarded to result from the d-d transition of $Cr^{3+}$. Then, the fluorescence spectrum of the phosphor of Example 6 was a spectrum that can be regarded to form a band spectrum across the whole of the wavelength range of 700 nm or more and 800 nm or less. Note that a peak wavelength of the fluorescence spectrum in the phosphor of Example 6 was 735 nm.

Moreover, as seen from FIG. 15, the phosphor of Example 6 had intense excitation bands in a wavelength range of 400 nm or more and 500 nm or less and a wavelength range of 580 nm or more and 680 nm or less. That is, the phosphor of Example 6 was a phosphor that intensely absorbs purple to blue-green light and orange to dark red light and emits fluorescence.

The above represents that the phosphor of Example 6 is excited by a solid-state light emitting element that emits at least one type of light selected from purple, blue, blue green, orange, red, and dark red. Then, the above represents that the phosphor of Example 6 can perform wavelength conversion for the excitation light into fluorescence that forms a band spectrum across the whole of the wavelength range of 700 nm or more and 800 nm or less. Note that a full width at half maximum in the fluorescence spectrum of the phosphor of Example 6 was approximately 100 m.

Next, a wavelength converter including the phosphor of Example 7 was fabricated, and fluorescence characteristics thereof were evaluated. Specifically, first, the phosphor of Example 7 was formed into a pellet shape by using a hand press, whereby a wavelength converter was fabricated. Subsequently, the obtained wavelength converter was excited by laser light, and energy (radiant flux of fluorescence) of fluorescence radiated from the wavelength converter at that time was measured. At this time, a central wavelength of the laser light was set to 445 nm. Moreover, energy of the laser light was changed from 0.93 W to 3.87 W. A power meter was used for evaluating the energy of the laser light. Moreover, an integrating sphere was used for evaluating the energy of the fluorescence emitted from the wavelength converter.

TABLE 1

| Energy of laser light (W) | Energy density of laser light (W/mm$^2$) | Energy of wavelength-converted light (mW) |
| --- | --- | --- |
| 0.93 | 0.73 | 199 |
| 1.67 | 1.31 | 346 |
| 2.4 | 1.89 | 484 |
| 3.14 | 2.46 | 610 |
| 3.87 | 3.04 | 700 |

In Table 1, energy of the fluorescence radiated from the wavelength converter when the energy of the laser light is changed from 0.93 W to 3.87 W is shown. For reference, an energy density of the laser light is also shown in Table 1.

As shown in Table 1, light with energy of 0.1 W or more was emitted from the wavelength converter. Then, even when the energy of the laser light was increased from 0.93 W to 3.87 W, the wavelength converter radiated light with high energy. That is, it has been found out that the $Cr^{3+}$-activated phosphor can maintain high light emission efficiency even in a region where the energy of the excitation light is high. This result is largely different from the conventional technical common sense that it is essential to use a phosphor with a short afterglow (less than 10 µs) in order to suppress saturation of the fluorescence output, and is surprising. Moreover, when consideration is taken for the case where the phosphor generates heat to raise a temperature of the phosphor when the phosphor is excited by the laser light with high energy, it can also be said that the phosphor of Example 7 is an excellent phosphor in which such a temperature rise gives less reduction to light emission efficiency.

Figure 16:
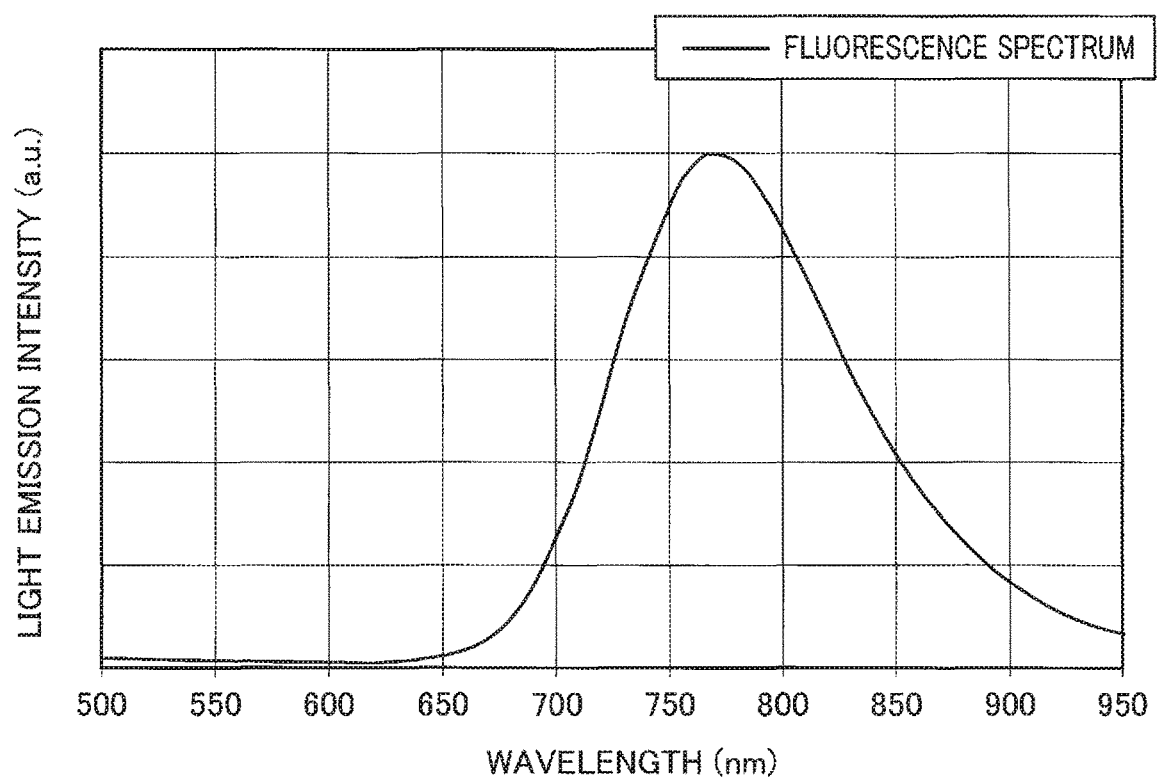
FIG. 16 is a graph illustrating a light emission spectrum of a phosphor used in a light emitting device of Example 7.

FIG. 16 is a fluorescence spectrum when the wavelength converter including the phosphor of Example 7 was excited by the laser light with energy of 3.87 W. The fluorescence spectrum of wavelength converter including the phosphor of Example 7 was a broad spectrum that can be regarded to result from the d-d transition of $Cr^{3+}$. Then, this fluorescence spectrum was a spectrum that can be regarded to form a band spectrum across the whole of the wavelength range of 700 nm or more and 800 nm or less. Note that a peak wavelength of the fluorescence spectrum when the wavelength converter including the phosphor of Example 7 was excited by the laser light with energy of 3.87 W was 767 nm. Moreover, a full width at half maximum of a peak of this fluorescence spectrum was approximately 100 nm.

Although the contents of this embodiment have been described above in accordance with the Examples, it is obvious to those skilled in the art that this embodiment is not limited to the description of these and that various modifications and improvements are possible.

The entire contents of Japanese Patent Application No. 2018-61256 (filed on: Mar. 28, 2018) and Japanese Patent Application No. 2018-191630 (filed on: Oct. 10, 2018) are incorporated herein by reference.

INDUSTRIAL APPLICABILITY

In accordance with the present disclosure, there can be provided an endoscope light emitting device capable of efficiently exciting the fluorescent drug even if the variation of characteristics occurs and radiating high-output near-infrared light, an endoscope using the light emitting device, and a fluorescence imaging method.

REFERENCE SIGNS LIST 1, 1A, 1B, 1C Endoscope light emitting device
2 Solid-state light emitting element
3, 3A Wavelength converter
4 First phosphor
6 Primary light
7 First wavelength-converted light
8 Second phosphor
9 Second wavelength-converted light
11 Endoscope

The invention claimed is:

1. An endoscope light emitting device comprising:
a solid-state light emitting element; and
a wavelength converter including a first phosphor that emits a first wavelength-converted light,
wherein the first wavelength-converted light has a light component across at least a whole of a wavelength range from 700 nm to 800 nm,
wherein the first wavelength-converted light has a fluorescence peak within a wavelength range from 600 nm to 800 nm, and
wherein the endoscope light emitting device is used for a fluorescence imaging method.

2. The endoscope light emitting device according to claim 1, wherein the first wavelength-converted light has a light component across a whole of a wavelength range from 600 nm to 800 nm.

3. The endoscope light emitting device according to claim 1, wherein the wavelength converter further includes a second phosphor that absorbs the primary light emitted by the solid-state light emitting element and emits a second wavelength-converted light that is visible light.

4. The endoscope light emitting device according to claim 3, wherein the first phosphor emits the first wavelength-converted light by absorbing at least one of the primary light and the second wavelength-converted light.

5. The endoscope light emitting device according to claim 3,
wherein a peak of the fluorescence emitted by the second phosphor remains within a wavelength range from 500 nm to 700 nm, and
wherein the solid-state light emitting element includes a blue laser element as an excitation source.

6. The endoscope light emitting device according to claim 1, wherein the first phosphor includes at least one of a $Eu^{2+}$-activated phosphor and a $Ce^{3+}$-activated phosphor.

7. The endoscope light emitting device according to claim 1, wherein the solid-state light emitting element radiates a laser light having a maximum intensity value within a wavelength range from 430 nm to 480 nm, from 500 nm to 560 nm, or from 600 nm to 700 nm.

8. An endoscope comprising the endoscope light emitting device according to claim 1.

9. The endoscope according to claim 8, further comprising a detector that detects fluorescence emitted from a fluorescent drug that has absorbed the first wavelength-converted light.

10. A fluorescence imaging method using the endoscope according to claim 8, the fluorescence imaging method comprising:
administering a fluorescent drug to a subject; and
applying the first wavelength-converted light to the subject with whom the fluorescent drug has made contact.

11. A fluorescence imaging method using the endoscope light emitting device according to claim 1, the fluorescence imaging method comprising:
administering a fluorescent drug to a subject; and
applying the first wavelength-converted light to the subject with whom the fluorescent drug has made contact.

* * * * *